(12) United States Patent
Bernard et al.

(10) Patent No.: US 8,318,445 B2
(45) Date of Patent: Nov. 27, 2012

(54) IMMUNOMAGNETIC CAPTURE AND IMAGING OF BIOLOGICAL TARGETS

(75) Inventors: Bruce J-C Bernard, Austin, TX (US); Kurt D. Hoffacker, Austin, TX (US); Charles J. Collins, Austin, TX (US)

(73) Assignee: Luminex Corporation, Austin, TX (US)

( * ) Notice: Subject to any disclaimer, the term of this patent is extended or adjusted under 35 U.S.C. 154(b) by 817 days.

(21) Appl. No.: 12/349,811

(22) Filed: Jan. 7, 2009

(65) Prior Publication Data

US 2009/0176255 A1 Jul. 9, 2009

Related U.S. Application Data

(60) Provisional application No. 61/019,482, filed on Jan. 7, 2008.

(51) Int. Cl.
*G01N 33/553* (2006.01)
*G01N 33/569* (2006.01)

(52) U.S. Cl. ...... 435/7.2; 435/7.24; 435/7.31; 435/7.32; 435/971; 435/973; 436/526; 436/806

(58) Field of Classification Search ......................... None
See application file for complete search history.

(56) References Cited

U.S. PATENT DOCUMENTS

| | | | |
|---|---|---|---|
| 4,230,685 A | 10/1980 | Senyei et al. | 436/526 |
| 5,736,330 A | 4/1998 | Fulton | 435/6 |
| 5,981,180 A | 11/1999 | Chandler et al. | 435/6 |
| 5,993,665 A | 11/1999 | Terstappen et al. | 210/695 |
| 6,057,107 A | 5/2000 | Fulton | 435/6 |
| 6,265,229 B1 | 7/2001 | Fodstad et al. | 436/526 |
| 6,268,222 B1 | 7/2001 | Chandler et al. | 436/523 |
| 6,449,562 B1 | 9/2002 | Chandler et al. | 702/19 |
| 6,514,295 B1 | 2/2003 | Chandler et al. | 8/607 |
| 6,524,793 B1 | 2/2003 | Chandler et al. | 435/6 |
| 6,528,165 B2 | 3/2003 | Chandler | 428/402.2 |
| 6,773,812 B2 | 8/2004 | Chandler et al. | 428/403 |
| 7,282,180 B2 * | 10/2007 | Tibbe et al. | 422/82.05 |
| 2006/0024756 A1 | 2/2006 | Tibbe et al. | 435/7.2 |
| 2006/0159962 A1 | 7/2006 | Chandler et al. | 428/403 |
| 2006/0216696 A1 | 9/2006 | Goguen | 435/7.32 |
| 2007/0064990 A1 | 3/2007 | Roth | 382/128 |
| 2007/0281311 A1 | 12/2007 | Roth et al. | 435/6 |

FOREIGN PATENT DOCUMENTS

| | | | |
|---|---|---|---|
| WO | WO 99/45094 | * | 9/1999 |
| WO | WO 2006/041453 | | 4/2006 |
| WO | WO 2007/133465 | | 11/2007 |

OTHER PUBLICATIONS

Dynal, "Cell separation and protein purification," *Dynal Technical Handbook*, 2nd Edition, 1996.
Olsvik et al., "Magnetic separation techniques in diagnostic microbiology," *Clinical Microbiology Reviews*, 7(1):43-54, 1994.
PCT International Search Report and Written Opinion, issued in International application No. PCT/US2009/030281, mailed Mar. 4, 2009.

* cited by examiner

*Primary Examiner* — David A Saunders
(74) *Attorney, Agent, or Firm* — Fulbright & Jaworski L.L.P.

(57) ABSTRACT

The present invention relates to methods and systems for labeling, isolating, detecting, and/or enumerating a statistically significant number of biological cells, or other biological analytes of interest, present in a complex matrix sample. The isolation of a biological target of interest from a sample mixture is done by immunomagnetic separation. Upon introduction of the sample within an imaging chamber, the capture complex (biological target-magnetic capture agent) will be attracted by the magnetic field and will lay on the surface of the chamber in the focal plane of the imaging system.

22 Claims, 12 Drawing Sheets

Field of View ("Label 1" Detection Channel)

T1

T2

Tn

T final

"Label 1" Detection Channel
Total Lymphocyte Count

"Label 2" Detection Channel
Absolute CD4 Count

"Label 3" Detection Channel
Absolute CD8 Count

IMMUNOMAGNETIC CAPTURE AND IMAGING OF BIOLOGICAL TARGETS

This application claims priority to U.S. Provisional Patent Application Ser. No. 61/019,482, filed Jan. 7, 2008. The entirety of the above-referenced disclosure is incorporated by reference.

BACKGROUND OF THE INVENTION

A. Field of the Invention

The present invention relates generally to the detection of biological analytes such as cells, spores, or bacteria. More particularly, the present invention concern the immunomagnetic isolation and fluorescent detection of biological analytes that can be present in a wide range of concentrations and that may be located in a complex biological or environmental sample matrix.

B. Description of Related Art

The study, characterization and census of biological cells have always depended on the use of imaging tools that allow for the visualization of what the naked eye could not see directly. Since the first scientific observation of cells reported in 1665 by Robert Hooke (The Cell—A molecular approach; Geoffrey M. Cooper. ASM Press. 1997), the field of microscopy has enabled the field of cell biology. From the basic early bright field light microscopes to the most recent scanning electron microscopes, cell biologists exploited the increasing magnifications and resolution capabilities of these technologies. Today, the integration of digital imaging with these powerful microscopes has expanded the scope of this field even more. Microscopy can now be combined with powerful image processing techniques for the rapid and automated analysis of a wide variety of samples.

While the imaging capabilities of microscopes have evolved over centuries, sample preparation is usually still a discrete task performed prior to imaging. Usually a targeted element of interest in the sample (the nucleus of a cell, or the membrane of a cell, etc. . . . ) is stained or dyed in order to enable its visualization. There is no integrated apparatus that would perform all needed steps of an analysis such as the preparation of a sample, the imaging and characterization of a target cell, and then the regeneration of the imaging chamber after analysis of the sample. Microscope glass slides and cover slips are still widely used to accommodate samples due to their simplicity of use and low cost. Many lab-on-a-chip techniques use some form of microscopy (bright field or fluorescent microscopy) and imaging approach as a detector; however, there is often a lack of integration around the compact imaging chamber. In this respect, many lab-on-a-chip devices are still their infancy. Scanning electron microscope (SEM) instruments also lack sample preparation automation, and each sample is required to be individually mounted on a pin and coated with a metal prior to analysis. Microscopy systems therefore suffer from a lack of throughput. Sample preparation, positioning of the sample onto the focal plane and localization of the area of interest remain laborious processes.

The characterization of cells (size, shape) characterization of markers on the surface of cells can also be done by flow cytometry. Since the late 1970s, flow cytometry has enabled scientists to analyze a variety of cell types and offers numerous advantages over other cell-based techniques including: speed, preservation of cell viability and cellular functions, and simultaneous measurements of multiple cellular parameters.

The appeal of flow cytometry arises from the flexibility and sensitivity of fluorescence technology combined with the technique's high speed and powerful data integration capabilities. Flow cytometry currently is the gold standard method for cell sorting and analysis (Bioinformatics Market Research 2006 Report #06-030: "influencing brand preference in the flow cytometry market"). While Flow cytometers improve throughput of cell analysis, they are expensive and technically challenging to operate. Even the most affordable flow cytometer models are priced over $100,000, and more sophisticated models are priced at over $300,000. In addition, flow cytometers require well-trained operators and are very sensitive to shifts in their optical alignment. Consequently the overall purchasing and operating costs of these instruments make them inaccessible to many laboratories, particularly those located in resource-poor countries. Furthermore, flow systems are typically designed to take measurements from a single particle at a time, thus increasing the time required to collect images from multiple particles.

SUMMARY OF THE INVENTION

In one embodiment, the present invention provides a method for immobilizing and detecting a biological target in a sample comprising: (a) contacting a sample with a magnetic capture agent having a specific affinity for a particular epitope on the biological target that may be present in the sample; (b) contacting the sample with a first labeling agent having a specific affinity for a particular epitope on the biological target; (c) introducing an aliquot of the sample into a chamber; (d) applying a magnetic field to the chamber to attract the magnetic capture agent to a surface of the chamber; (e) detecting and enumerating the biological targets that are immobilized on the surface of the chamber by binding to the magnetic capture agent, and labeled by binding to the labeling agent; and (f) detecting and enumerating the immobilized and labeled biological target. In certain embodiments, the method further comprises determining whether a statistically significant number of the labeled biological targets are immobilized on the surface of the chamber and introducing one or more additional aliquots of the sample into the chamber until a statistically significant number of the labeled biological targets are immobilized on the surface of the chamber. In certain embodiments, the method further comprises determining whether the number of the labeled biological targets immobilized on the surface of the chamber exceeds a maximum threshold and, if the maximum threshold is exceeded, then cleaning the imaging chamber and introducing one or more smaller aliquots of the sample into the chamber until a number of labeled biological targets that is statistically significant but below the maximum threshold is immobilized on the surface of the chamber. In certain embodiments, the method further comprising recording the count of biological targets detected.

The magnetic capture agent and the labeling agent may have a specific affinity for the same epitope or for different epitopes. The sample may be contacted with the magnetic capture agent prior to introducing the sample into the chamber or after introducing the sample into the chamber. The sample may be contacted with the labeling agent prior to introducing the sample into the chamber or after introducing the sample into the chamber. In certain aspects of the invention, the sample maybe contacted with additional magnetic capture agents, such as a second, third, fourth, fifth, sixth, seventh, eighth, ninth, tenth, twentieth, fiftieth or more magnetic capture agent, having a specific affinity for a different epitope than the first capture agent. The different epitope may be on the same biological target as the epitope recognized by the first capture agent or it may be on a different biological target. In certain aspects of the invention, the sample maybe contacted with additional labeling agents, such as a second, third, fourth, fifth, sixth, seventh, eighth, ninth, tenth or more labeling agent, having a specific affinity for a particular epitope on the biological target, wherein the additional labeling agents are labeled with a label different than the label of the first labeling agent. In some embodiments, the first labeling agent and the second, third, fourth, fifth, etc. labeling agent have specific affinity to different epitopes present on different biological target populations.

In another embodiment, the present invention provides a method for immobilizing and detecting one or more biological target populations and/or subpopulations in a sample comprising: (a) contacting a sample with a magnetic capture agent having a specific affinity for a particular epitope on a biological target population that may be present in the sample; (b) contacting the sample with a first labeling agent having a specific affinity for a particular epitope on the biological target population; (c) contacting the sample with a second labeling agent having a specific affinity for a particular epitope on a first subpopulation of biological targets in the biological target population; (d) contacting the sample with a third labeling agent having a specific affinity for a particular epitope on a second subpopulation of biological targets in the biological target population; (e) introducing an aliquot of the sample into a chamber; (f) applying a magnetic field to the chamber to attract the magnetic capture agent to a surface of the chamber; (g) detecting and enumerating the biological targets that are immobilized on the surface of the chamber by binding to the magnetic capture agent, and labeled by binding to the first labeling agent; (h) detecting and enumerating the immobilized biological target labeled with each of the first, second, and third labeling agent. In certain embodiments, the method further comprises determining whether a statistically significant number of the labeled biological targets are immobilized on the surface of the chamber and introducing one or more additional aliquots of the sample into a chamber until a statistically significant number of the labeled biological targets are immobilized on the surface of the chamber.

In certain aspects, the methods further comprise correlating the number of biological targets detected with the number of biological targets in the sample. The correlating may comprise, for example, determining a concentration of the biological target in the sample and/or determining the total number of biological targets in the sample. Where two or more different biological targets are assayed, the methods may further comprise determining a ratio of the first population or subpopulation of biological targets to a second population or subpopulation of biological targets. The method may also comprise calculating the percentage of a first subpopulation of biological targets in a population biological targets. The method may further comprise calculating the percentage of a second, third, fourth, fifth, sixth, seventh, eighth, ninth, tenth or more subpopulation of cells in the cell population.

In some embodiments, the methods further comprising performing a washing step prior to the detection and enumeration of the biological targets in the imaging chamber in order to remove components of a sample that have not been immobilized by the magnetic field. The washing step may be performed prior to each detection and enumeration in the sample loading process or it may be performed only prior to the final detection and enumeration step.

The biological target may be any biological target of interest. In particular embodiments the biological target is a cell. The cell may be, for example, a eukaryotic cell or a prokaryotic cell. Eukaryotic cells include, but are not limited to, mammalian cells, fish cells, amphibian cells, avian cells, reptilian cells, insect cells, plant cells, or fungus cells. In certain aspects of the invention, the cells are lymphocytes, leukocytes or monocytes. The prokaryotic cells may be, for example, bacteria cells or bacterial spores or any other biological analyte of interest known to the ones skilled in the art. Where the biological target is a cell, the epitopes detected by the capture agents and labeling agents are preferably epitopes on the surface of the cell. For example, if the biological target is a T cell, the epitopes may be one or more of CD3, CD4, CD8, CD45, CD38, and/or CD70.

The biological target may be in a sample. A sample may be any composition containing a cell or suspected of containing a cell. In certain aspects of the invention, the sample may be a bodily fluid (including but not limited to whole blood, serum, saliva, urine, sperm) obtained from a subject, such as a human. In some aspects of the invention the subject has or is suspected of having a disease. For example, the subject may have a disease caused by a bacterial or viral infection. In one embodiment, the subject has or is suspected of having an HIV infection. In other aspects of the invention, the sample is an environmental sample such as, for example, a soil, water, or air sample, or other substances found in one's surroundings.

The capture agents may be antibodies, aptamers, nucleic acid probes such as but not limited to DNA or RNA, proteins, or any other molecule, natural or synthesized, that binds specifically to a biological target of interest. The capture agents are magnetically responsive by being coupled to magnetic particles. For example, the capture agents may be coupled to carboxy-functionalized magnetic particles. The magnetic particles may be magnetic, paramagnetic, or superparamagnetic. Multiple units of a capture agent may be used around the biological target to create a magnetic complex attractable by the magnetic field of the apparatus. The capture agent strategy may include the capture of a population of biological targets greater than the population of interest.

The labeling agent may be antibodies, aptamers, nucleic acid probes such as but not limited to DNA or RNA, proteins, or any other molecule, natural or synthesized, that binds specifically to a target analyte of interest. The labeling agents are detectable by the detecting apparatus because they are coupled to a reporter molecule, such as a fluorescent molecule or other biological label known to those in the art. Some biological targets that are captured by the capture agent and magnetic field may not be necessarily revealed by any labeling reagents.

A labeling agent, which may also be referred to as a reporter, is a molecule that facilitates the detection of a molecule to which it is attached. Direct reporter molecules include fluorophores, chromophores, and radiophores. Non-limiting examples of fluorophores include, a red fluorescent squarine dye such as 2,4-Bis[1,3,3-trimethyl-2-indolinylidenemethyl]cyclobutenediylium-1,3-dioxolate, an infrared dye such as 2,4 Bis [3,3-dimethyl-2-(1H-benz[e]indolinylidenemethyl)]cyclobutenediylium-1,3-dioxolate, or an orange fluorescent squarine dye such as 2,4-Bis[3,5-dimethyl-2-pyrrolyl]cyclobutenediylium-1,3-diololate. Additional non-limiting examples of fluorophores include quantum dots, Alexa Fluor® dyes, AMCA, BODIPY® 630/650, BODIPY® 650/665, BODIPY®-FL, BODIPY®-R6G, BODIPY®-TMR, BODIPY®-TRX, Cascade Blue®, CyDye™, including but not limited to Cy2™, Cy3™, and Cy5™, a DNA intercalating dye, 6-FAM™, Fluorescein, HEX™, 6-JOE, Oregon Green® 488, Oregon Green® 500, Oregon Green® 514, Pacific Blue™, REG, phycobilliproteins including, but not limited to, phycoerythrin and allophycocyanin, Rhodamine Green™, Rhodamine Red™, ROX™, TAMRA™, TET™, Tetramethylrhodamine, or Texas Red®. A signal amplification reagent, such as tyramide (PerkinElmer), may be used to enhance the fluorescence signal. Indirect reporter molecules include biotin, which must be bound to another molecule such as streptavidin-phycoerythrin for detection. Pairs of labels, such as fluorescence resonance energy transfer pairs or dye-quencher pairs, may also be employed.

The present invention also provides kits that provide various components that may be used in connection with the methods disclosed herein. In one embodiment, the kit may comprise one or more magnetic capture agents and one or more labeling agents. In certain aspects, the kit comprises a magnetic antibody having a specific affinity for a particular epitope on biological target and a labeling agent having a specific affinity for a particular epitope on biological target.

In one embodiment, the present invention provides a system for performing immunogenic capture and imaging of biological targets. In certain aspects, the system comprises: an imaging system; labeling agents and magnetic capture agents adapted to be introduced into the imaging system, the labeling agents and magnetic capture agents having specific affinity for particular epitopes on biological target(s); a magnet for selectively introducing a magnetic field to the imaging system for immobilizing the magnetic capture agents and any biological targets and labeling agents bound thereto.

It is contemplated that any method or composition described herein can be implemented with respect to any other method or composition described herein.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1A:
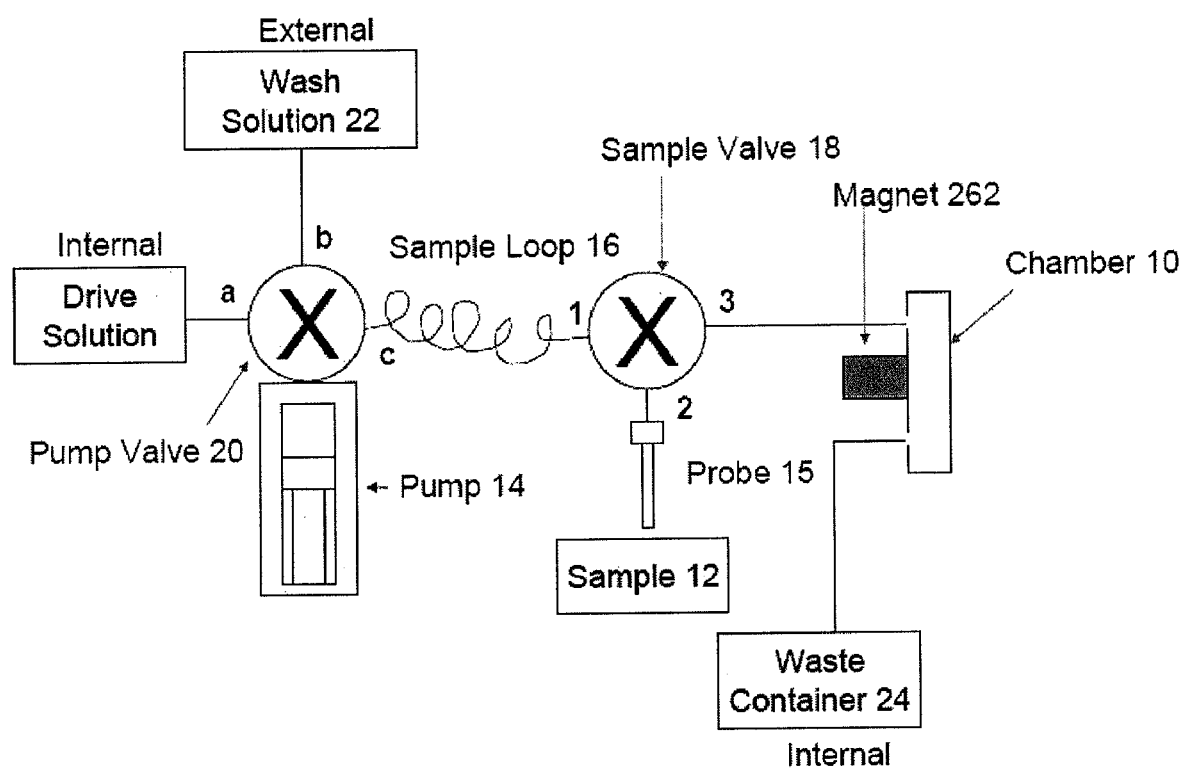
FIGS. 1A, 1B, and 1C show block diagrams of fluid handling systems.

The present invention relates to methods and systems for labeling, isolating, detecting, and/or enumerating a statistically significant number of biological cells, or other biological analytes of interest, present in a complex matrix sample. The isolation of a biological target of interest from a sample mixture is done by immunomagnetic separation. Magnetic capture agents with a specific affinity for a particular epitope on the biological target of interest will bind to the biological target rendering it magnetically responsive. Upon introduction of the sample within the apparatus imaging chamber, the capture complex (biological target-magnetic capture agent) will be attracted by the magnetic field and will lay on the surface of the chamber in the focal plane of the imaging system. The rest of the sample (non-magnetic) is preferably washed away from the imaging chamber. The methods may be implemented on imaging systems such as those described herein and on the apparatus described application Ser. No. 11/757,841 entitled: "Systems and methods for performing measurements of one or more materials," which is incorporated herein by reference.

The biological targets are also labeled directly within the sample using detection agents, such as fluorescently labeled antibodies. The labeling of the biological targets allows the visualization of the captured biological targets using the optical and imaging functionality of the apparatus. Because of the multiplex capability of the apparatus (multiple excitation lights sources and multiple detection channels), identification of multiple populations of biological targets is possible—for example, one biological target with multiple labels (the biological target belongs to multiple populations or subpopulations) or different biological targets with unique labels (each biological target belongs to a unique population or subpopulation).

The enumeration of the isolated and labeled biological targets is typically done by differentiating fluorescent objects from a dark background in the imaging chamber and by applying image processing algorithms to identify and count biological targets based on their size, radius, roundness and other relevant measurements.

The introduction of the sample into the imaging chamber may be monitored in real time. This capability of the apparatus enables the adjustment of the sample size in order to isolate a statistically significant number of biological targets. Samples with low concentration of biological targets will be loaded in the imaging chamber in greater quantity than a typical sample. Alternatively, samples with high concentration of biological targets will be loaded in lesser quantity. Upon completion of the sample loading step, all targeted populations of biological targets will be enumerated using image processing algorithms. At the end of the analysis, the removal of the magnetic field will allow for a complete wash and regeneration of the imaging chamber, if desired.

Concentrations of the biological targets in the sample can be calculated by enumerating the biological targets within the field of view of the imaging chamber by knowing the total volume of sample loaded in the apparatus, the ratio of the area of the field of view to the total area of the imaging chamber, and the capture efficiency. Once the biological targets are being loaded into the imaging chamber, they will be captured due to the presence of the magnetic field. For a specific application, the system and method need to be characterized in such a way that the capture efficiency of the apparatus for the biological targets of interest will be known. In addition, the imaging chamber will be fully characterized as well in such a way that the imaged field of view will represent a known subset of the total surface area of the chamber. The image processing algorithms will enable the enumeration of the cells within the field of view, and depending on the number of cells detected, the algorithm will command for additional sample to be loaded or will instead trigger a washing sequence.

The capture efficiency represents the percentage of biological targets captured in the chamber from the total number of biological targets loaded in the chamber. There are many factors influencing the capture efficiency. Where the biological target is a cell, these factors may include: the number of receptors (or markers) available on the surface of the cell of interest; the number of magnetic particles bound at the surface, the affinity of the capture agent (e.g., an antibody) for a specific receptor as well as the incubation time and the concentration of the reagents; the strength of the magnetic field; the size and depth of the chamber; the viscosity of the sample; and the velocity of the sample when traveling through the chamber.

There are two independent objectives related to capture efficiency: maximization and characterization. Maximizing the capture efficiency will enable the use of a smaller sample size. It will lower the limit of detection for qualitative assays (such as the detection of anthrax spores in environmental samples) where the objective is to detect the presence or absence of a certain cell, bacteria or spore, and not to quantify a concentration within the sample. By forcing the sample into a smaller imaging chamber, the probability of having the analyte of interest in the field of view increases and therefore the limit of detection improves. For quantitative assays, the objective is not only to detect the presence or absence of a certain target, but also to quantify a concentration of the target within the sample. In this instance, the capture efficiency needs to be characterized and consistent in order to be able to correlate the number of targets (e.g., cells) detected to the actual number of targets (e.g., cells) in the sample. The capture efficiency can be characterized and measured by using a standard sample with a known amount of a biological target (e.g., a particular population of cells), loading the sample into the imaging chamber, and measuring how many of the biological target can be detected. The detected number of biological targets can then be compared to the actual numbers of biological targets to calculate the capture efficiency.

An alternate method, based on the traditional analytical method of "the added volumes," involves making aliquots of the sample and adding to each aliquot a known amount of the biological target before any sample processing step. The measurement of the biological target of each aliquot enables the creation of a standard curve that includes the capture efficiency (and any other variations in the sample processing protocol, or from the sample) in its intrinsic parameter. Measurement of the biological target in the sample can then be extrapolated to the standard curve to calculate the cell concentration in the sample. This method will be of particular interest for samples where the cell concentration is so low that even if the entire sample is loaded, there would not be enough cells captured to be statistically significant. By adding a known amount of cells and creating a standard curve, this method enables the measurements of a concentration below the threshold defined by more conventional methods.

The imaging chamber also has an impact on the ability to efficiently capture biological targets, and its design can be tailored to specific applications. For applications where the total sample size is minimal and where the potential number of biological targets to be capture is low, the capture efficiency needs to be maximized and an imaging chamber with minimal dimension can be used. A small width and length of the chamber will mean that the captured biological targets will be dispersed on a smaller imaging surface, which will increase the density of cells within the field of view. In addition a thin chamber will subject biological targets to a lower gradient of magnetic forces and will keep the overall sample closer to the magnet. The closer the biological targets will be to the magnet, the stronger the attractive force of the magnetic field will be and the higher the capture efficiency will become. For applications where the sample size can be quite large and where a qualitative response is sufficient, the imaging chamber can be designed with larger dimension in order to process more sample within the same time frame and without having to increase the velocity of the sample introduction.

The magnification of the instrument can be modified and optimized for the detection of cells, spores or bacteria of different sizes: the bigger the analyte the less the needed magnification. The limiting factor for the detection of the target is the resolution of the overall optical path. In order to have an image processing algorithm capable of identifying an object and characterizing it efficiently according to size, shape or radius, the object size is preferably at least 5×5 pixels.

The image processing algorithm determines the number of biological targets from the raw images of the field of view. Each fluorescent object in the field of view will be identified against the background signal. Then each object will be characterized in terms of size (number of pixel wide and number of pixel long), roundness (define as the ratio of the square perimeter of the object divided by (4×Pi×Area of the object), and/or other measurement of interest deemed necessary (diameter, area, radius etc. . . . ). With this approach, non-specific fluorescent objects of random size and shape will be excluded from the total enumeration count. All remaining objects are included in the biological target count.

Once the initial detection and enumeration process is performed, an iterative process may be started before calculating a final concentration of cell in the sample. In this way, the number of targets (e.g., beads, cells or other biological targets) counted may be above a certain threshold to be considered statistically significant. A lower threshold of 30 is often used because normal distribution statistical analysis can be performed for sample sizes above 30. However, other lower thresholds, such as 35, 40, 45, or 50, can be used in order to minimize the impact of image processing and measurements errors. As an upper limit, the threshold can be defined by a predetermined number of targets, such as 100, 200, 300, 400, 500, or 1000 targets. The threshold can also be defined according to the number of doublets present in the field of view: as the number of targets in the field of view increases, the probability of having two targets overlapping increases and doublets occur more frequently. When the frequency of occurrence of doublets is no longer linear with respect to the sample volume being loaded, the upper limit threshold can be considered to have been reached.

When the number of targets is below the lower threshold, the image processing algorithm will instruct loading of additional sample before repeating the enumeration step. This iterative process will take place until the number of targets in the field of view reaches a pre-determined minimum threshold that is still below the upper threshold. Alternatively, the counts from separate enumerations, with a complete wash of the imaging chamber between enumerations, can be saved and then added together until the minimum threshold is met. If the upper threshold is exceeded, then the magnetic filed may be removed from the imaging chamber, the imaging chamber cleaned (e.g., by pushing drive/wash fluid through a by-pass line and through the chamber), and a smaller aliquot of the sample loaded into the imaging chamber. The final enumeration step will serve as the basis for any further calculation of concentration of cells.

While the minimum and maximum threshold strategy is attractive due to its simplicity, other strategies or other conditions can be defined and implemented in order to decide if the number of objects detected is sufficient. For instance, instead of having a maximum count defining a high count threshold, one can perform a simultaneous measurement of the size of the objects being counted. Highly concentrated samples would result in a significant overlap of many target objects. Unresolved, overlapping objects would be counted as a single object but their size will be characteristic of a large aggregate. Therefore enumerating the number of objects above a certain size and defining a maximum count for these large objects could also serve to identify a sample that is too concentrated.

The total volume of sample loaded in the chamber can be known due to the use of, for example, a precise syringe pump to pull the sample into a sample loop and to inject it into the main drive fluid line. This dual line approach enables the real-time dilution of the sample in order to slow down sample introduction but also to lower sample viscosity and improve capture efficiency. The drive fluid is in a buffer solution capable of diluting the sample. The drive fluid can be the same buffer as the washing buffer. By merging the sample line into the main drive fluid line, the drive fluid will effectively dilute the sample and carry it to the imaging chamber. Modifying the speed at which the sample is merged into the main drive fluid line will result into a different dilution factor. This enables the efficient loading of different volumes of sample, in particular small volumes.

If multiple populations and/or subpopulations of biological targets are analyzed simultaneously, multiple fluorescent labels or other reporter molecules can be used to differentiate between the different populations and/or subpopulations of biological targets. The calculations described in the previous paragraphs will be repeated for each detection channel used and for each population and/or subpopulation of biological target. In each calculation, the capture efficiency of the biological targets may be the same or different. In any case, like in single-plex mode, the capture efficiency needs to be characterized to enable a calculation of concentration of biological targets in the sample.

In order to confirm a consistent performance of the system a series of controls may be used and run prior to analyzing samples. Such controls may include a series of fluorescent magnetic microspheres such as Luminex MagPlex beads. The series of controls is built by creating microspheres with various content of magnetite. In order to differentiate them, each series of microspheres may be uniquely coded using for example the standard Luminex dyeing protocol. Other coding techniques such as but not limited to size difference, light scattering signature, light emission, light absorption could also be used by those skilled in the art to create distinct series on microspheres. Each series will then be defined by its code and expected capture efficiency and the instrument can be calibrated in order to have an actual capture efficiency matching the expected capture efficiency.

The series of microsphere controls can also be used to characterize the magnetization of the biological targets. By comparing the capture efficiency of the targets to the capture efficiency of the microsphere controls, the magnetite content around the targets can be evaluated against the magnetite content of the controls. The incubation time can then be optimized to ensure that there is enough magnetite content around the target while still keeping the entire assay within a reasonable amount of time.

A. Imaging Systems

FIGS. 1-6 are illustrative of various apparatus on which the methods described herein may be performed. It is noted that the figures are not drawn to scale. In particular, the scale of some of the elements of the figures is exaggerated to emphasize characteristics of the elements. Elements shown in more than one figure that may be similarly configured have been indicated using the same reference numerals. It is further noted that the description of these apparatus is illustrative only and is for the purpose of teaching those skilled in the art the general manner of carrying out the invention. Further modifications and alternative embodiments will be apparent to those skilled in the art in view of this description.

Figure 1B:
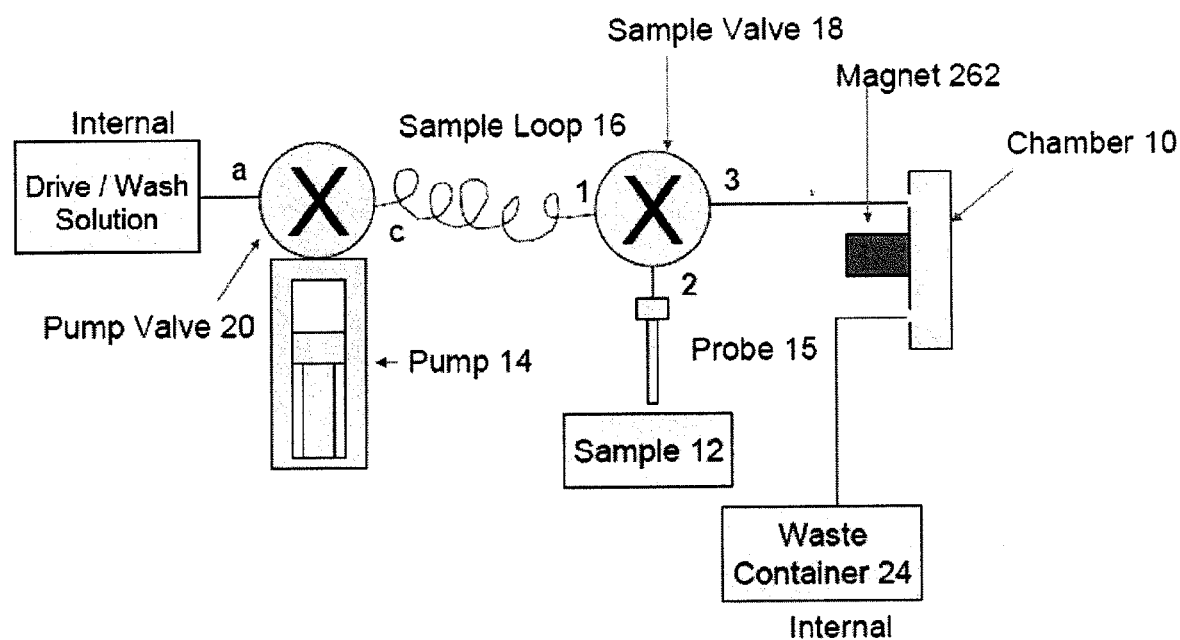
Figure 1C:
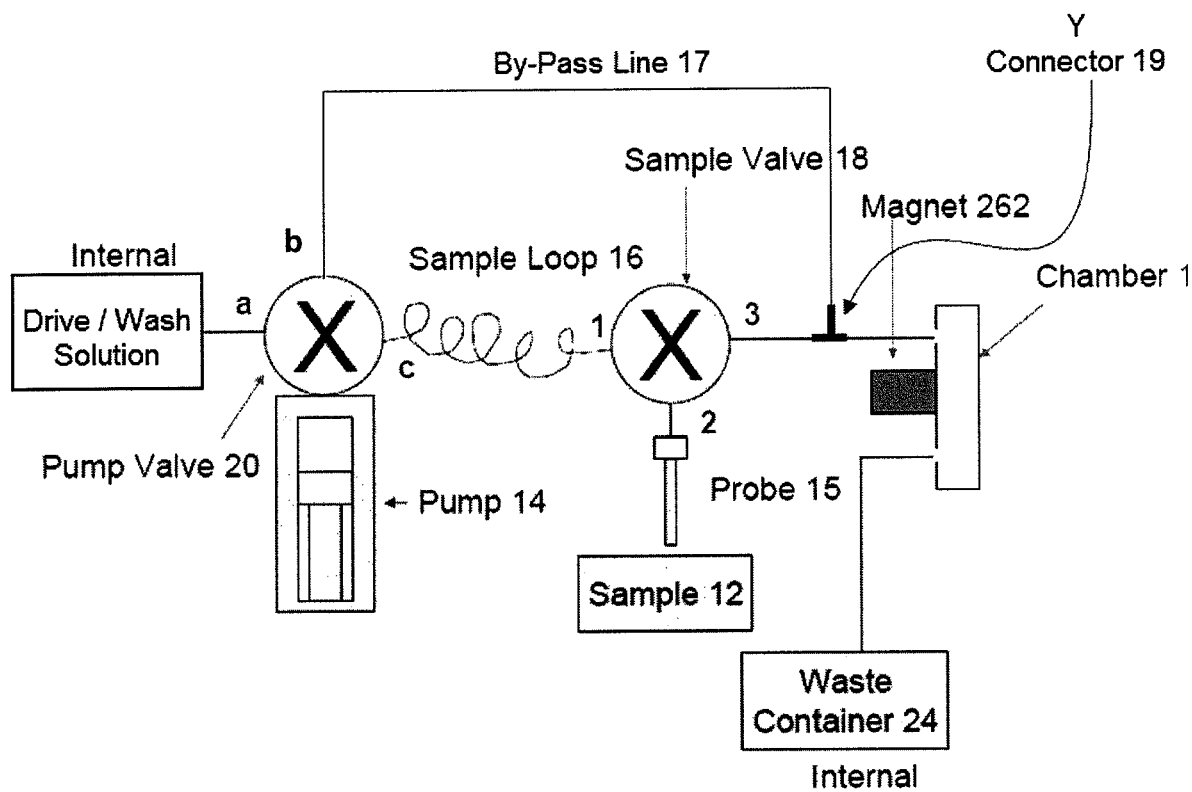
Figure 2:
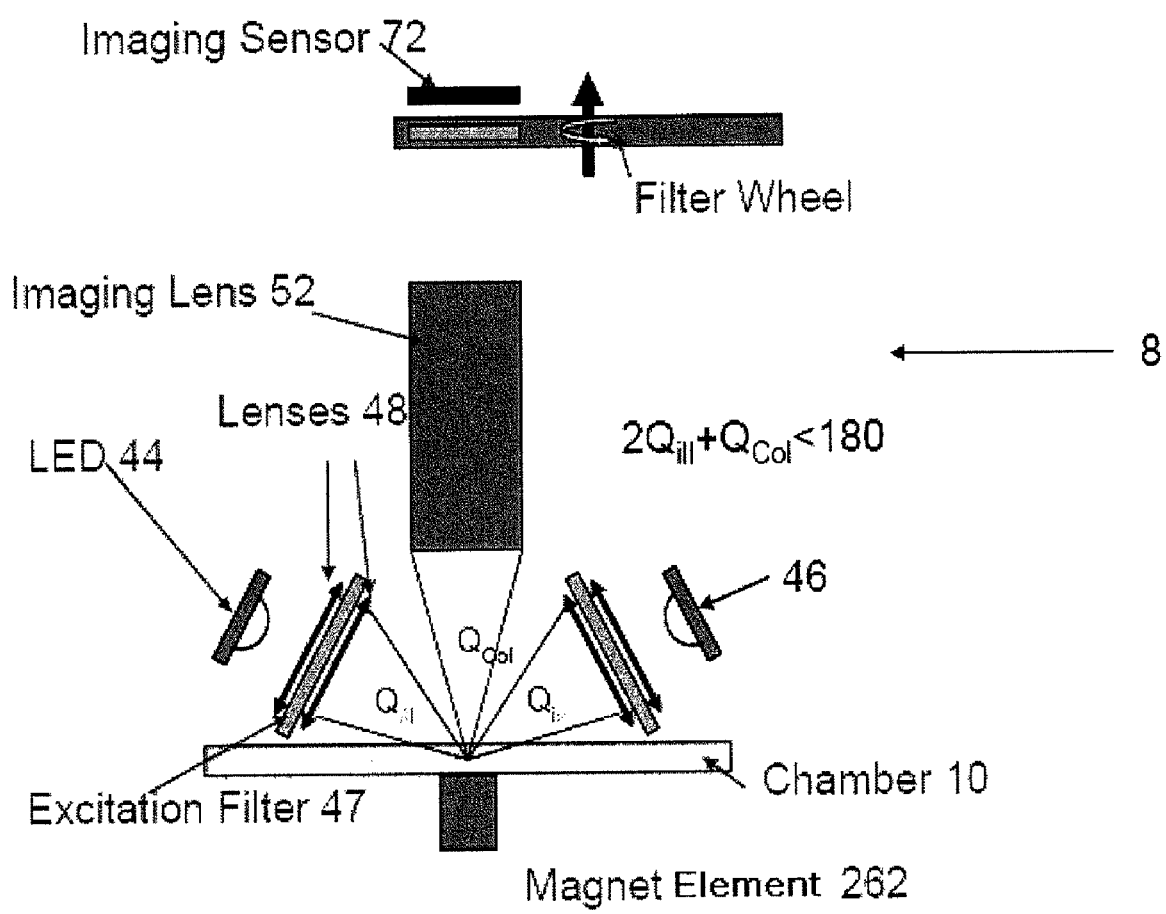
FIG. 2 is a block diagram of the optical configuration of an imaging device.

The embodiments illustrated in FIGS. 1A, 1B, 1C, and 2 relate generally to systems configured to transfer one or more materials to an imaging volume of a measurement device from one or more storage vessels. The systems have three major components: fluid handling, optic configuration, and particle immobilization subsystem. FIGS. 1A-C show the functional components of the fluid handling subsystem in three configurations, while FIG. 2 illustrates the functional components of the optics subsystem.

In the fluid handling subsystems of FIG. 1A-C, samples are transferred into imaging chamber 10 of the measurement device from sample storage vessel 12. The imaging volume may be configured as an imaging chamber 10, which may have any suitable configuration known in the art. Storage vessel 12 may be configured as a Vacutainer, centrifuge tube, injection syringe, micro titer plate or any other suitable sample container known in the art.

The system also includes a bi-directional pump 14 configured to draw fluid into a storage reservoir and to later expel fluid from the storage reservoir into the imaging volume of chamber 10. Pump 14 may have any suitable configuration known in the art. Since the biological targets are substantially immobilized during the exposure time as described further herein, pulse-free flow such as that obtained from an expensive syringe pump is not required. A sufficient reservoir can be formed out of a length of tubing 16 between pump 14 and sample valve 18. Such a reservoir is commonly called a "sample loop." The tubing may have any suitable configuration. The function of sample valve 18 is to connect a sample probe 15 to the reservoir (sample loop 16) when aspirating from sample storage vessel 12 and to connect the reservoir to the imaging chamber 10 when dispensing. Sample valve 18 may include any suitable valve known in the art.

Pump valve 20 is utilized at the pump end of the storage reservoir (Sample Loop 16). In FIG. 1A, pump valve 20 is connected to a drive solution storage vessel and a wash solution storage vessel. This configuration can be used if a drive solution and wash solution of different compositions are desired. However, the same solution may be used as the drive solution and the wash solution, in which case one storage vessel may be used. FIGS. 1B and 1C show pump valve 20 connected to a drive/wash solution storage vessel. FIG. 1C shows a by-pass line 17 that allows the wash of imaging chamber 10 after the introduction of a portion of the sample without having to use sample loop 16 where the rest of the sample is stored. The by-pass line thus enables the sequential loading of small aliquots from the same sample in sample loop 16 in order to accommodate for different sample concentrations and to extend the dynamic range of the method. Without by-pass line 17, washing and then loading additional sample in imaging chamber 10 involves a complete flush of sample loop 16 and then a further pickup of sample from sample storage vessel 12 to reload sample loop 16—while this approach is functional, it is less efficient and wastes more sample as compared to using a by-pass line. Pump valve 20 may include any suitable valve known in the art. In alternative embodiments, the pump and wash valves could be combined into a single valve. Pump 14 may also be configured to transfer the one or more materials and any other fluid in imaging chamber 10 to waste vessel 24. Waste vessel 24 may have any suitable configuration known in the art.

There are three primary modes of operating the fluid handling subsystem illustrated in FIGS. 1A-C to load a sample in the imaging chamber 10, namely a load procedure with sample wash, a load procedure without sample wash, and an iterative load procedure. In the fluid handling subsystem shown in FIG. 1A, the load procedure with no sample wash generally occurs as follows:

Clean System:
1) Pump Valve 20 to position a.
2) Load Drive Solution.
3) Pump Valve 20 to position c.
4) Sample Valve 18, move from position 1 to 3.
5) Move magnet 262 away from imaging chamber 10.
6) Push Drive Solution through chamber to clean chamber 10.
7) Sample Valve 18, position 1 to 2.
8) Push Drive solution through Probe 15 to clean Probe.

Load Sample:
1) Pump Valve 20 to position a.
2) Load Drive Solution.
3) Pump Valve 20 to position c.
4) Sample Valve 18, position 1 to 2.
5) Lower probe 15 into sample storage vessel 12.
6) Load a sample into sample loop 16.
7) Raise probe 15 and pull until air is at sample valve 18 and entire sample is in sample loop 16.
8) Sample Valve 18, position 1 to 3.
9) Move magnet 262 toward imaging chamber 10.
10) Push Sample from sample loop 16 into imaging chamber 10 capturing the magnetic capture agents and any biological targets and detection agents associated with them (capture complex).
11) Take Images with the capture complex is immobilized.

Clean System:
1) Pump Valve 20 to position a.
2) Load Drive Solution.
3) Pump Valve 20 to position c.
4) Sample Valve 18, position 1 to 3.
5) Move magnet 262 away from imaging chamber 10.
6) Push Drive Solution through chamber 10 to clean chamber.
7) Sample Valve 18, position 1 to 2.
8) Push Drive solution through Probe 15 to clean Probe.

In the fluid handling subsystem shown in FIG. 1A, the load procedure with sample wash generally occurs as follows:

Clean System:
1) Pump Valve 20 to position a.
2) Load Drive Solution.
3) Pump Valve 20 to position c.
4) Sample Valve 18, position 1 to 3.
5) Move magnet 262 away from chamber 10.
6) Push Drive Solution through chamber 10 to clean chamber.
7) Sample Valve 18, position 1 to 2.
8) Push Drive solution through Probe 15 to clean Probe.

Preload Wash Solution:
1) Pump Valve 20 to position b.
2) Load Wash Solution.
3) Pump Valve 20 to position c.
4) Sample Valve 18, position 1 to 3.
5) Push Wash Solution through chamber.
6) Sample Valve 18, position 1 to 2.
7) Push Wash solution through Probe 15 (sample loop 16 and probe 15 preloaded with Wash Solution).

Load Sample:
1) Pump Valve 20 to position a.
2) Load Drive Solution.
3) Pump Valve 20 to position c.
4) Sample Valve 18, position 1 to 2.
5) Lower probe 15 into well 12.
6) Load Sample into sample loop 16.
7) Raise probe 15 and pull until air is at sample valve and entire sample is in sample loop 16.
8) Sample Valve 18, position 1 to 3.
9) Move magnet 262 toward chamber 10.
10) Push Sample from sample loop 16 into chamber 10 capturing the magnetic capture agents and any biological targets and detection agents associated with them (capture complex).
11) Push Wash Solution in sample loop 16 behind sample over the capture complexes to "Wash" the capture complexes.
12) Take Images with the capture complexes immobilized.

Clean System:
1) Pump Valve 20 to position a.
2) Load Drive Solution.
3) Pump Valve 20 to position c.
4) Sample Valve 18, position 1 to 3.
5) Move magnet 262 away from chamber 10.
6) Push Drive Solution through chamber 10 to clean chamber.
7) Sample Valve 18, position 1 to 2.
8) Push Drive solution through Probe 15 to clean Probe.

In the fluid handling subsystem shown in FIG. 1A, the iterative load procedure generally occurs as follows:

Clean System:
1) Pump Valve 20 to position a.
2) Load Drive Solution.
3) Pump Valve 20 to position c.
4) Sample Valve 18, position 1 to 3.
5) Move magnet 262 away from chamber 10.
6) Push Drive Solution through chamber 10 to clean chamber.
7) Sample Valve 18, position 1 to 2.
8) Push Drive solution through Probe 15 to clean Probe.

Preload Wash Solution:
1) Pump Valve 20 to position b.
2) Load Wash Solution.
3) Pump Valve 20 to position c.
4) Sample Valve 18, position 1 to 3.
5) Push Wash Solution through chamber.
6) Sample Valve 18, position 1 to 2.
7) Push Wash solution through Probe 15 (sample loop 16 and probe 15 preloaded with Wash Solution).

Load Sample:
1) Pump Valve 20 to position a.
2) Load Drive Solution.
3) Pump Valve 20 to position c.
4) Sample Valve 18, position 1 to 2.
5) Lower probe 15 into well 12.
6) Load Sample into sample loop 16.
7) Raise probe 15 and pull until air is at sample valve and entire sample is in sample loop 16.
8) Sample Valve 18, position 1 to 3.
9) Move magnet 262 toward chamber 10.
10) Push Sample from sample loop 16 into chamber 10 capturing the magnetic capture agents and any biological targets and detection agents associated with them (capture complex).
11) Push Wash Solution in sample loop 16 behind sample over the capture complexes to "Wash" the capture complexes.
12) Take Images with the capture complexes immobilized.
13) Process images using image analysis algorithms and determine if further sample needs to be loaded. If further sample needs to be loaded, then restart loading sequence at step 1. If further sample is not needed, then proceed to "Clean System" sequence.

Clean System:
1) Pump Valve 20 to position a.
2) Load Drive Solution.
3) Pump Valve 20 to position c.
4) Sample Valve 18, position 1 to 3.
5) Move magnet 262 away from chamber 10.
6) Push Drive Solution through chamber 10 to clean chamber.
7) Sample Valve 18, position 1 to 2.
8) Push Drive solution through Probe 15 to clean Probe.

In the fluid handling subsystem shown in FIG. 1B, the load procedure with no sample wash generally occurs as follows:

Clean System:
1) Pump Valve 20 to position a.
2) Load Drive/Wash Solution.
3) Pump Valve 20 to position c.
4) Sample Valve 18, move from position 1 to 3.
5) Move magnet 262 away from imaging chamber 10.
6) Push Drive/Wash Solution through chamber to clean chamber 10.
7) Sample Valve 18, position 1 to 2.
8) Push Drive/Wash Solution through Probe 15 to clean Probe.

Load Sample:
1) Pump Valve 20 to position a.
2) Load Drive/Wash Solution.
3) Pump Valve 20 to position c.
4) Sample Valve 18, position 1 to 2.
5) Lower probe 15 into sample storage vessel 12.
6) Load a sample into sample loop 16.
7) Raise probe 15 and pull until air is at sample valve 18 and entire sample is in sample loop 16.
8) Sample Valve 18, position 1 to 3.
9) Move magnet 262 toward imaging chamber 10.
10) Push Sample from sample loop 16 into imaging chamber 10 capturing the magnetic capture agents and any biological targets and detection agents associated with them (capture complex).
11) Take Images with the capture complex is immobilized.

Clean System:
1) Pump Valve 20 to position a.
2) Load Drive/Wash Solution.
3) Pump Valve 20 to position c.
4) Sample Valve 18, position 1 to 3.
5) Move magnet 262 away from imaging chamber 10.
6) Push Drive/Wash Solution through chamber 10 to clean chamber.
7) Sample Valve 18, position 1 to 2.
8) Push Drive/Wash Solution through Probe 15 to clean Probe.

In the fluid handling subsystem shown in FIG. 1B, the load procedure with sample wash generally occurs as follows:

Clean System:
1) Pump Valve 20 to position a.
2) Load Drive/Wash Solution.
3) Pump Valve 20 to position c.
4) Sample Valve 18, position 1 to 3.
5) Move magnet 262 away from chamber 10.
6) Push Drive/Wash Solution through chamber 10 to clean chamber.
7) Sample Valve 18, position 1 to 2.
8) Push Drive solution through Probe 15 to clean Probe.

Load Sample:
1) Pump Valve 20 to position a.
2) Load Drive/Wash Solution.
3) Pump Valve 20 to position c.
4) Sample Valve 18, position 1 to 2.
5) Lower probe 15 into well 12.
6) Load Sample into sample loop 16.
7) Raise probe 15 and pull until air is at sample valve and entire sample is in sample loop 16.
8) Sample Valve 18, position 1 to 3.
9) Move magnet 262 toward chamber 10.
10) Push Sample from sample loop 16 into chamber 10 capturing the magnetic capture agents and any biological targets and detection agents associated with them (capture complex).
11) Push Drive/Wash Solution in sample loop 16 behind sample over the capture complexes to "Wash" the capture complexes.
12) Take Images with the capture complexes immobilized.

Clean System:
1) Pump Valve 20 to position a.
2) Load Drive/Wash Solution.
3) Pump Valve 20 to position c.
4) Sample Valve 18, position 1 to 3.
5) Move magnet 262 away from chamber 10.
6) Push Drive/Wash Solution through chamber 10 to clean chamber.
7) Sample Valve 18, position 1 to 2.
8) Push Drive solution through Probe 15 to clean Probe.

In the fluid handling subsystem shown in FIG. 1B, the iterative load procedure generally occurs as follows:

Clean System:
1) Pump Valve 20 to position a.
2) Load Drive/Wash Solution.
3) Pump Valve 20 to position c.
4) Sample Valve 18, position 1 to 3.
5) Move magnet 262 away from chamber 10.
6) Push Drive/Wash Solution through chamber 10 to clean chamber.
7) Sample Valve 18, position 1 to 2.
8) Push Drive/Wash Solution through Probe 15 to clean Probe.

Load Sample:
1) Pump Valve 20 to position a.
2) Load Drive/Wash Solution.
3) Pump Valve 20 to position c.
4) Sample Valve 18, position 1 to 2.
5) Lower probe 15 into well 12.
6) Load Sample into sample loop 16.
7) Raise probe 15 and pull until air is at sample valve and entire sample is in sample loop 16.
8) Sample Valve 18, position 1 to 3.
9) Move magnet 262 toward chamber 10.
10) Push Sample from sample loop 16 into chamber 10 capturing the magnetic capture agents and any biological targets and detection agents associated with them (capture complex).
11) Push Drive/Wash Solution in sample loop 16 behind sample over the capture complexes to "Wash" the capture complexes.
12) Take Images with the capture complexes immobilized.
13) Process images using image analysis algorithms and determine if further sample needs to be loaded. If further sample needs to be loaded, then restart loading sequence at step 1. If further sample is not needed, then proceed to "Clean System" sequence.

Clean System:
1) Pump Valve 20 to position a.
2) Load Drive/Wash Solution.
3) Pump Valve 20 to position c.
4) Sample Valve 18, position 1 to 3.
5) Move magnet 262 away from chamber 10.
6) Push Drive/Wash Solution through chamber 10 to clean chamber.
7) Sample Valve 18, position 1 to 2.
8) Push Drive/Wash solution through Probe 15 to clean Probe.

In the fluid handling subsystem shown in FIG. 1C, the load procedure with no sample wash generally occurs as follows:

Clean System:
1) Pump Valve 20 to position a.
2) Load Drive/Wash Solution.
3) Pump Valve 20 to position c.
4) Sample Valve 18, move from position 1 to 3.
5) Move magnet 262 away from imaging chamber 10.
6) Push Drive/Wash Solution through chamber to clean chamber 10.
7) Sample Valve 18, position 1 to 2.
8) Push Drive/Wash Solution through Probe 15 to clean Probe.

Load Sample:
1) Pump Valve 20 to position a.
2) Load Drive/Wash Solution.
3) Pump Valve 20 to position c.
4) Sample Valve 18, position 1 to 2.
5) Lower probe 15 into sample storage vessel 12.
6) Load a sample into sample loop 16.
7) Raise probe 15 and pull until air is at sample valve 18 and entire sample is in sample loop 16.
8) Sample Valve 18, position 1 to 3.
9) Move magnet 262 toward imaging chamber 10.
10) Push Sample from sample loop 16 into imaging chamber 10 capturing the magnetic capture agents and any biological targets and detection agents associated with them (capture complex).
11) Take Images with the capture complex is immobilized.

Clean System:
1) Pump Valve 20 to position a.
2) Load Drive/Wash Solution.
3) Pump Valve 20 to position c.
4) Sample Valve 18, position 1 to 3.
5) Move magnet 262 away from imaging chamber 10.
6) Push Drive/Wash Solution through chamber 10 to clean chamber.
7) Sample Valve 18, position 1 to 2.
8) Push Drive/Wash Solution through Probe 15 to clean Probe.

In the fluid handling subsystem shown in FIG. 1C, the load procedure with sample wash generally occurs as follows:

Clean System:
1) Pump Valve 20 to position a.
2) Load Drive/Wash Solution.
3) Pump Valve 20 to position c.
4) Sample Valve 18, position 1 to 3.
5) Move magnet 262 away from chamber 10.
6) Push Drive/Wash Solution through chamber 10 to clean chamber.
7) Sample Valve 18, position 1 to 2.
8) Push Drive solution through Probe 15 to clean Probe.

Load Sample:
1) Pump Valve 20 to position a.
2) Load Drive/Wash Solution.
3) Pump Valve 20 to position c.
4) Sample Valve 18, position 1 to 2.
5) Lower probe 15 into well 12.
6) Load Sample into sample loop 16.
7) Raise probe 15 and pull until air is at sample valve and entire sample is in sample loop 16.
8) Sample Valve 18, position 1 to 3.
9) Move magnet 262 toward chamber 10.
10) Push Sample from sample loop 16 into chamber 10 capturing the magnetic capture agents and any biological targets and detection agents associated with them (capture complex).
11) Pump Valve 20 to position a.
12) Load Drive/Wash Solution.
13) Pump Valve 20 to position b.
14) Push Drive/Wash Solution through By-Pass Line 17 and over the capture complexes in Image Chamber 10 to "Wash" the capture complexes.
15) Take Images with the capture complexes immobilized.

Clean System:
1) Pump Valve 20 to position a.
2) Load Drive/Wash Solution.
3) Pump Valve 20 to position c.
4) Sample Valve 18, position 1 to 3.
5) Move magnet 262 away from chamber 10.
6) Push Drive/Wash Solution through chamber 10 to clean chamber.
7) Sample Valve 18, position 1 to 2.
8) Push Drive solution through Probe 15 to clean Probe.

In the fluid handling subsystem shown in FIG. 1C, the iterative load procedure generally occurs as follows:

Clean System:
1) Pump Valve 20 to position a.
2) Load Drive/Wash Solution.
3) Pump Valve 20 to position c.
4) Sample Valve 18, position 1 to 3.
5) Move magnet 262 away from chamber 10.
6) Push Drive/Wash Solution through chamber 10 to clean chamber.
7) Sample Valve 18, position 1 to 2.
8) Push Drive/Wash Solution through Probe 15 to clean Probe.

Load Sample:
1) Pump Valve 20 to position a.
2) Load Drive/Wash Solution.
3) Pump Valve 20 to position c.
4) Sample Valve 18, position 1 to 2.
5) Lower probe 15 into well 12.
6) Load Sample into sample loop 16.
7) Raise probe 15 and pull until air is at sample valve and entire sample is in sample loop 16.
8) Sample Valve 18, position 1 to 3.
9) Move magnet 262 toward chamber 10.
10) Push Sample from sample loop 16 into chamber 10 capturing the magnetic capture agents and any biological targets and detection agents associated with them (capture complex).
11) Pump Valve 20 to position a.
12) Load Drive/Wash Solution.
13) Pump Valve 20 to position b.
14) Push Drive/Wash Solution through By-Pass Line 17 and over the capture complexes in Image Chamber 10 to "Wash" the capture complexes.
15) Take Images with the capture complexes immobilized.
16) Process images using image analysis algorithms and determine if further sample needs to be loaded. If further sample needs to be loaded in chamber 10, then restart loading sequence at step 10 if additional Sample is still contained in sample loop 16 or at step 1 if additional Sample needs to first be loaded into sample loop 16. If further sample is not needed in chamber 10, then proceed to "Clean System" sequence.

Clean System:
1) Pump Valve 20 to position a.
2) Load Drive/Wash Solution.
3) Pump Valve 20 to position c.
4) Sample Valve 18, position 1 to 3.
5) Move magnet 262 away from chamber 10.
6) Push Drive/Wash Solution through chamber 10 to clean chamber.
7) Sample Valve 18, position 1 to 2.
8) Push Drive/Wash solution through Probe 15 to clean Probe.

An advantage of using the sample wash and iterative loading procedures where the sample is "washed" is to remove from the surrounding solution detection agents that are not bound to a biological target. For the convenience of processing, some assays do not perform the wash step, which typically results in a higher "background" signal when the assay response from biological targets is measured.

The optics subsystem 8 is broadly illustrated in FIG. 2. Subsystem 8 includes magnetic element 262 positioned on the side of imaging chamber 10 opposite the optics of the system. Magnetic element 262 may include any suitable magnetic element known in the art such as a permanent magnet or an electromagnet that can be used to generate a suitable magnetic field. In this manner, biological targets bound to magnetic capture complexes can be substantially immobilized in imaging chamber 10 using a magnetic field generated by magnetic element 262 at the side of the chamber. Although magnetic element 262 is shown adjacent to imaging chamber 10 in FIG. 2, the magnetic element may be coupled to imaging chamber 10, integral in imaging chamber 10, or spaced from the imaging chamber 10. In addition, although FIG. 2 shows one magnetic element positioned proximate the imaging chamber, it is to be understood that the system may include more than one magnetic element.

After signal acquisition by the measurement device, the magnetic field may be removed (e.g., by using a solenoid to move a permanent magnet or by turning an electromagnet on and off with a switch), and the biological targets may exit the imaging chamber 10.

The simplest imaging chamber 10 design is an imaging chamber that has a relatively smooth internal surface on the side of the imaging chamber proximate the magnetic element such that the beads are randomly distributed across this internal surface as the magnet 262 pulls them to the surface. However, the imaging chamber 10 can also be designed to "hold" the capture complexes in particular spots when the magnetic field is applied as described in more detail herein.

With the capture complexes immobilized in the chamber 10, the illumination module (LEDs 44, 46) is operated to excite the detection agent, which in this embodiment is labeled with a fluorophore. The imaging sensor 72 (CCD) captures the image and the image is processed (See, e.g. U.S. patent application Ser. No. 11/534,166 entitled "Methods and Systems for Image Data Processing" filed Sep. 21, 2006 by Roth, which is incorporated by reference herein.) The magnet 262 releases the sample and the device is cleaned.

The position of the imaging sensors 72 in relation to the LEDs 44, 46, chamber 10 and magnet 262 can be adjusted for imaging biological targets in accordance with the present invention. In this embodiment, the detection agents have distinct characteristics, namely the dyes attached to the detection agents, that absorb and re-emit photons in no preferred direction (uniformly over all angles). The positions of the illumination by the LED's 44, 46 and imaging sensors (CCD 72) is chosen to optimize the "angle space" of any detection agents bound to biological targets in the Field of View (FOV) of the imaging sensors (CCD 72). Since the magnet 262 is on the back of the chamber 10, the angle space available for the illumination and imaging systems is a hemisphere above the magnet. The more coverage over this illumination angle space by the illumination optics (LEDs 44, 46), the more power imparted on the detection agents during imaging. Similarly, the higher the collection angle (Numerical Aperture) over the illumination angle space, the more flux the imaging lens 52 (FIG. 2) can collect and deliver to the imaging sensor 72 (CCD detector). A balance must be made between the angles allocated for the imaging sensors and the illumination system.

For low-cost manufacturability, the imaging lens 52 practical limit for numerical aperture is around 0.3 for a magnification of 4. For higher magnifications, the numerical aperture of imaging lens 52 could increase while maintaining the same cost guidelines. Other factors that effect the cost of the lens 52 are Field of View and broadness of waveband. A numerical aperture of 0.3 is roughly 35 degrees full angle.

For the positioning of the illumination module, e.g. the LEDs 44, 46, the limit may be the LED's brightness as well as the cost of the excitation filters 47. The etendue of the LED will dictate what of the detection agent's angle space is needed to provide the maximum LED flux over the field of view (FOV). (Etendue is the Area of the source multiplied by the solid angle of the source: it defines the geometry characteristics of the emitted flux.) If the FOV is relatively large, the angle space required will be lower and therefore more LEDs can be used.

Figure 3:
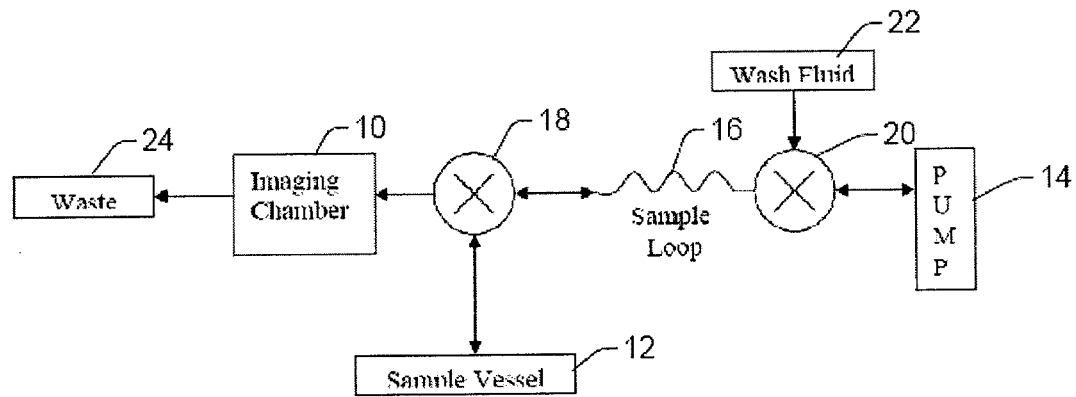
FIG. 3 shows a block diagram of an imaging system.

Another embodiment of such a system in accordance with the present invention is shown in FIG. 3. In this embodiment, samples are transferred into imaging volume 10 from storage vessel 12. The system also includes single bi-directional pump 14 configured to draw fluid into a storage reservoir and to later expel fluid from the storage reservoir into the imaging volume. Pump 14 may have any suitable configuration known in the art. Since the capture complexes are substantially immobilized during the exposure time as described further herein, pulse-free flow such as that obtained from an expensive syringe pump is not required for the system embodiments described herein. A sufficient reservoir can be formed out of a length of tubing 16 between pump 14 and sample valve 18. Such a reservoir is commonly called a "sample loop." Pump valve 20 is utilized at the pump end of the storage reservoir to allow fresh water (or other suitable reagent) from storage vessel 22 to flow to the imaging volume. Pump valve 20 may include any suitable valve known in the art. Note that the sample and pump valves could be combined into a single valve (not shown). Pump 14 may also be configured to transfer the one or more materials and any other fluid in imaging volume 10 to waste vessel 24. Waste vessel 24 may have any suitable configuration known in the art.

Figure 4:
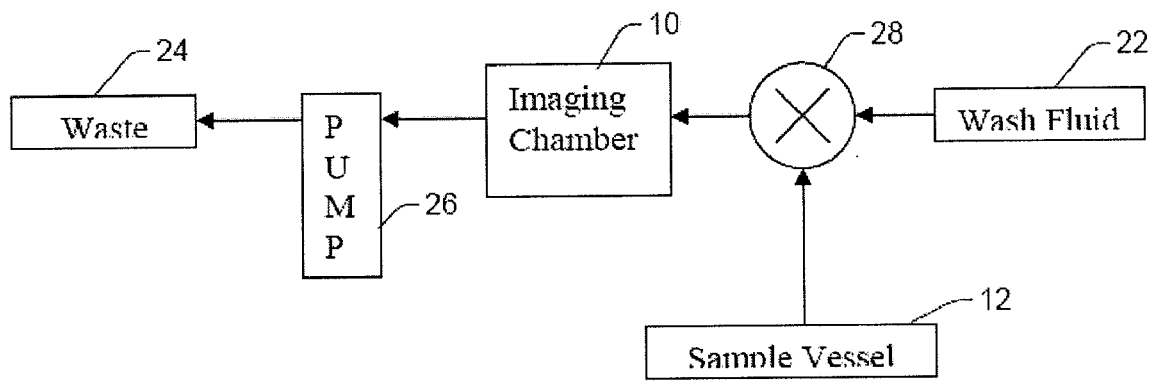
FIG. 4 shows a block diagram of an imaging system.

Another embodiment of a system configured to transfer one or more materials to an imaging volume of a measurement device from one or more storage vessels is shown in FIG. 4. In this configuration, the system includes pump 26 configured to draw liquid directly into imaging volume 10 from sample vessel 12 and then out to waste vessel 24. Pump 26 may include any suitable pump known in the art such as a peristaltic pump. Imaging volume 10, sample vessel 12, and waste vessel 24 may be configured as described above. Optional valve 28 between sample vessel 12 and wash fluid vessel 22 and imaging volume 10 may be configured to change positions depending on whether sample is to be transferred to the imaging volume or if wash fluid is to be transferred to the imaging volume (e.g., if the wash function is to be performed). Valve 28 may include any suitable valve known in the art. In addition, storage vessel 22 may be configured as described above. The embodiment shown in FIG. 4 differs from the embodiment shown in FIG. 3 since this embodiment does not include a temporary reservoir, includes one less valve, and utilizes a pump configured to move fluids in only one direction.

Figure 5:
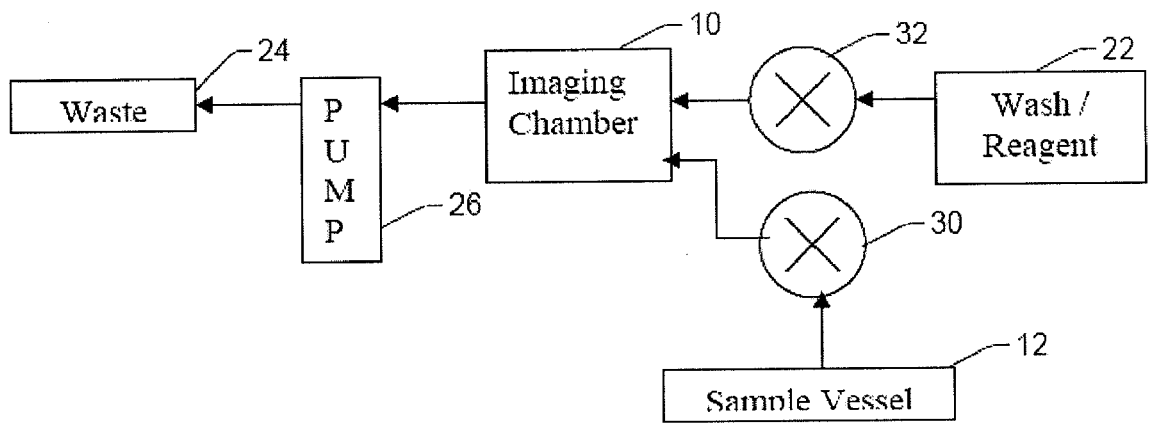
FIG. 5 shows a block diagram of an imaging system.

An additional embodiment of a system configured to transfer one or more materials to an imaging volume of a measurement device from one or more storage vessels is shown in FIG. 5. This embodiment has a configuration that is similar to the configuration of the embodiment shown in FIG. 4, with the exception that sample/wash valve 28 of the embodiment shown in FIG. 4 is replaced by two valves 30 and 32. Valves 30 and 32 may include any suitable valves known in the art. For example, valves 30 and 32 may include open/closed type valves configured to separately and simultaneously allow fluid from storage vessels 12 and 22, respectively, to be transferred into imaging volume 10. Storage vessels 12 and 22 and imaging volume 10 may be configured as described herein.

Providing separate wash and sample paths (i.e., one path from storage vessel 12 to imaging volume 10 and another separate path from storage vessel 22 to imaging volume 10) in this manner makes it possible to achieve all of the aspects of the embodiment shown in FIG. 4 and adds the ability to mix wash fluid and/or one or more reagents to the sample to be measured as the sample is transferred into imaging volume 10. Mixing wash fluid and/or one or more reagents to the sample as the sample is transferred to the imaging volume may be performed to dilute the sample such that the capture complexes are distributed farther apart within the imaging volume (e.g., farther apart on the surface of the imaging chamber).

Figure 6:
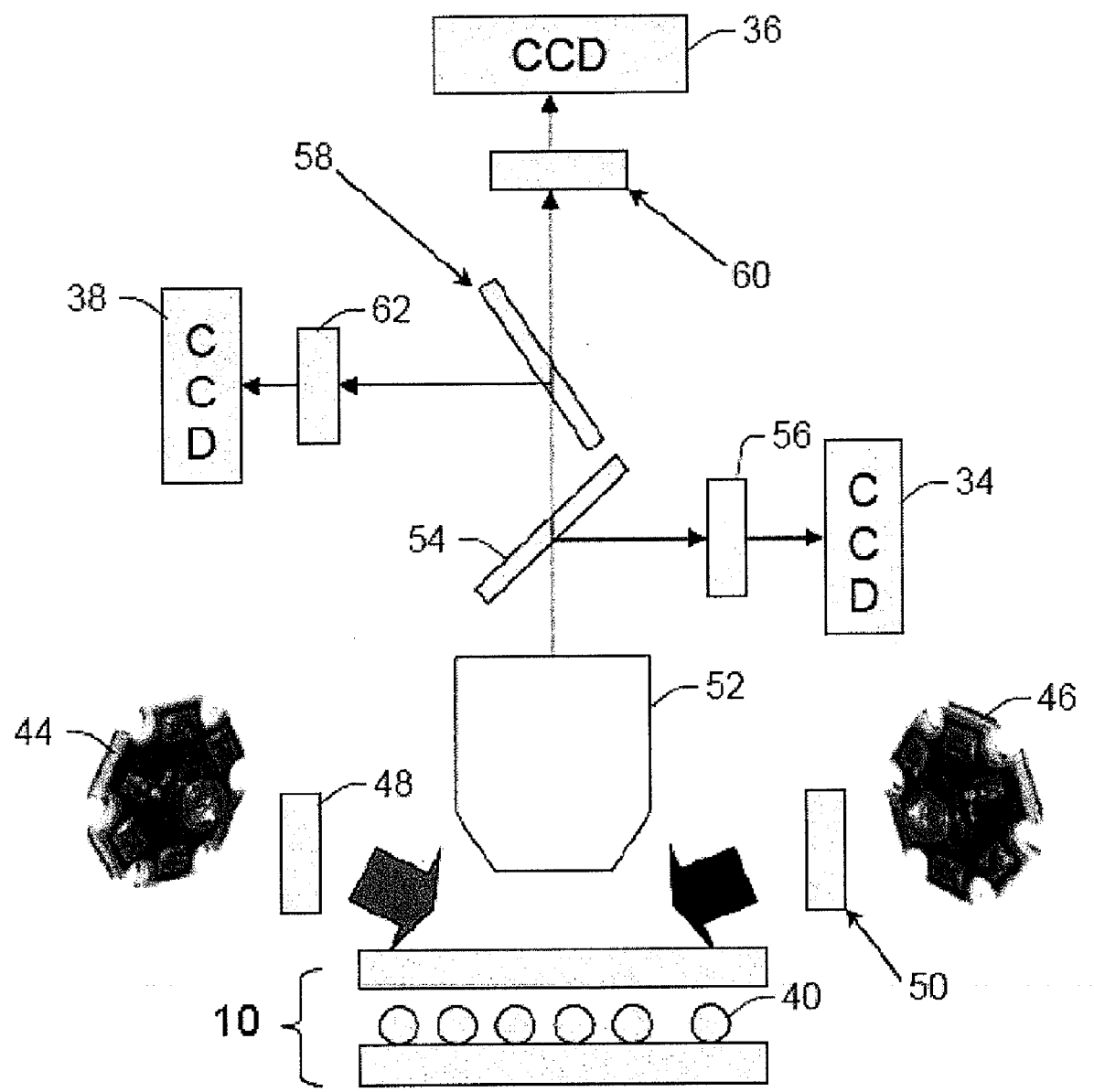
FIG. 6 is a schematic diagram illustrating a side view of the imaging system.

FIG. 6 illustrates one embodiment of a system configured to image one or more materials in an imaging volume of a measurement device. This system embodiment includes detectors 34, 36, and 38. Detectors 34, 36, and 38 may be CCD cameras or any other suitable imaging devices known in the art. Each of the detectors may have the same configuration or different configurations. Each of the detectors may be configured to detect light (e.g., light fluoresced from capture complexes 40 in imaging volume defined by imaging chamber 10) at a different wavelength or wavelength band. In addition, each of the detectors may be configured to generate images or "capture fluorescent pictures" of capture complexes 40 in imaging chamber 10.

The system also includes light sources 44 and 46 configured to emit light having different wavelengths or different wavelength bands (e.g., one of the light sources may be configured to emit red light and the other light source may be configured to emit green light). The light emitted by light sources 44 and 46 may include, for example, light in any part of the ultraviolet, visible, or near infrared wavelength spectrum. Light sources 44 and 46 may include LEDs or any other suitable light sources known in the art. Light sources 44 and 46 are arranged above the periphery of imaging chamber 10. In addition, the light sources are arranged above the imaging chamber such that each light source directs light to capture complexes 40 in imaging chamber 10 at different directions.

The system also includes filters 48 and 50 coupled to light sources 44 and 46, respectfully. Filters 48 and 50 may be bandpass filters or any other suitable spectral filters known in the art. In this manner, the system may use light sources 44 and 46 and filters 48 and 50 to sequentially illuminate the capture complexes with different wavelengths or different wavelength bands of light.

The system may also include lens 52 positioned at the center (or approximately the center) of the illumination "ring." Lens 52 may include any suitable refractive optical element known in the art. Lens 52 is configured to image light scattered and/or fluoresced from the capture complexes onto one or more monochrome CCD detector(s) (e.g., detectors 34, 36, and 38) via one or more optical elements, which may include one or more dichroic and one or more optical bandpass filters. For example, light exiting lens 52 is directed to dichroic filter 54, which may include any suitable dichroic optical element known in the art. Dichroic filter 54 is configured to reflect light of one wavelength or wavelength band and to transmit light of other wavelengths or wavelength bands. Light reflected by dichroic filter 54 is directed to filter 56, which may be a bandpass filter or other suitable spectral filter. Light exiting filter 56 is directed to detector 34.

Light transmitted by lens 52 may also be directed to dichroic filter 58, which may include any suitable dichroic optical element known in the art. Dichroic filter 58 may be configured to reflect light of one wavelength or wavelength band and to transmit light of other wavelengths or wavelength bands. Light transmitted by dichroic filter 58 is directed to filter 60, which may be a bandpass filter or other suitable spectral filter. Light exiting filter 60 is directed to detector 36. Light reflected by dichroic filter 58 is directed to filter 62, which may be a bandpass filter or other suitable spectral filter. Light exiting filter 62 is directed to detector 38. Furthermore, although the system shown in FIG. 6 includes two light sources, it is to be understood that the system may include any suitable number of light sources. Additionally, although the system shown in FIG. 6 includes three detectors configured to image light scattered and/or fluoresced from the capture complexes at different wavelengths or wavelength bands, it is to be understood that the system may include two or more detectors. For example, the system may include two or more CCD detectors (and optionally fixed filters) that can be used to simultaneously measure the classification channel(s) and reporter channel(s) thereby providing higher throughput for the measurements.

The system shown in FIG. 6 is, therefore, configured to generate a plurality or series of images representing the fluorescent emission of capture complexes 40 at several wavelengths of interest. In addition, the system may be configured to supply a plurality or series of digital images representing the fluorescence emission of the capture complexes to a processor (i.e., a processing engine). The system may or may not include the processor (not shown). The processor may be configured to acquire (e.g., receive) image data from detectors 34, 36, and 38. For example, the processor may be coupled to detectors 34, 36, and 38 in any suitable manner known in the art (e.g., via transmission media (not shown), each coupling one of the detectors to the processor, via one or more electronic components (not shown) such as analog-to-digital converters, each coupled between one of the detectors and the processor, etc.).

The processor may be configured to process and analyze these images to, for example, classify and enumerate the captured biological target(s). This information may be output by the processor in any suitable format such as a data array with an entry for fluorescent magnitude for each capture complex for each wavelength. Specifically, the processor may be configured to perform one or more steps of a method for processing and analyzing the images. Examples of methods for processing and analyzing images generated by a system such as that shown in FIG. 6 are illustrated in U.S. patent application Ser. No. 11/534,166 entitled "Methods and Systems for Image Data Processing" filed Sep. 21, 2006 by Roth, which is incorporated by reference herein. The systems described herein may be further configured as described in this patent application. In addition, the methods described herein may include any step(s) of any of the method(s) described in this patent application.

For example, in one embodiment the processor may be configured to analyze the images to detect and enumerate the biological targets (e.g., cells) that are immobilized on the surface of the chamber by binding the capture agent (e.g., magnetic antibody) and labeled by binding a detection agent (e.g., labeled antibody), and determine whether a statistically significant number of the labeled biological targets are immobilized on the surface of the chamber. The processor is configured such that it then prompts the addition of more sample into the chamber if a statistically significant number of the labeled biological targets were not immobilized on the surface of the chamber. The processor repeats the detection, enumeration, determination, and sample addition process until a statistically significant number of the labeled biological targets are immobilized on the surface of the chamber. The processor then proceeds with further processing and analysis of the image(s). As mentioned above, the processor is configured such that it then prompts the addition of more sample into the chamber if a statistically significant number of the labeled biological targets were not immobilized on the surface of the chamber. The processor may prompt the addition of more sample by prompting (such as by an audible or visual signal) a user to manually inject or operate a pump to deliver additional sample to the chamber. Alternatively, the pump may be under the control of the processor such that the pump operates to deliver additional sample to the chamber by receiving a signal from the processor.

The processor may be a processor such as those commonly included in a typical personal computer, mainframe computer system, workstation, etc. In general, the term "computer system" may be broadly defined to encompass any device having one or more processors, which executes instructions from a memory medium. The processor may be implemented using any other appropriate functional hardware. For example, the processor may include a digital signal processor (DSP) with a fixed program in firmware, a field programmable gate array (FPGA), or other programmable logic device (PLD) employing sequential logic "written" in a high level programming language such as very high speed integrated circuits (VHSIC) hardware description language (VHDL). In another example, program instructions (not shown) executable on the processor to perform one or more steps of the computer-implemented methods described in the above-referenced patent application may be coded in a high level language such as C#, with sections in C++ as appropriate, ActiveX controls, JavaBeans, Microsoft Foundation Classes ("MFC"), or other technologies or methodologies, as desired. The program instructions may be implemented in any of various ways, including procedure-based techniques, component-based techniques, and/or object-oriented techniques, among others.

Program instructions implementing methods such as those described in the above-referenced patent application may be contained in a computer-readable medium such as a read-only memory, a random access memory, a magnetic or optical disk, or a magnetic tape.

B. Antibodies

Methods for preparing and characterizing antibodies are well known in the art. Briefly, a polyclonal antibody is prepared by immunizing an animal with an immunogen comprising a polypeptide of interest and collecting antisera from that immunized animal. A wide range of animal species can be used for the production of antisera. Typically an animal used for production of anti-antisera is a non-human animal including rabbits, mice, rats, hamsters, pigs, goats, or horses. Because of the relatively large blood volume of rabbits, a rabbit is a preferred choice for production of polyclonal antibodies.

The immunogenicity of a particular immunogen composition can be enhanced by the use of non-specific stimulators of the immune response, known as adjuvants. Exemplary adjuvants include complete Freund's adjuvant (a non-specific stimulator of the immune response containing killed Mycobacterium tuberculosis), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

MAbs may be readily prepared through use of well-known techniques, such as those exemplified in U.S. Pat. No. 4,196, 265, incorporated herein by reference. Typically, this technique involves immunizing a suitable animal with a selected immunogen composition. The immunizing composition is administered in a manner effective to stimulate antibody producing cells. Rodents such as mice and rats are commonly used for monoclonal antibody production.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody producing B lymphocytes from the immunized animal are then fused with cells of an immortal myeloma cell, generally one of the same species as the animal that was immunized. Myeloma cell lines suited for use in hybridoma producing fusion procedures preferably are non-antibody producing, have high fusion efficiency, and enzyme deficiencies that render then incapable of growing in certain selective media which support the growth of only the desired fused cells (hybridomas).

Methods for generating hybrids of antibody producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion procedures usually produce viable hybrids at low frequencies. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas are then serially diluted and cloned into individual antibody producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

C. Aptamers

Aptamers are nucleic acid sequences that are designed through repeated rounds of selection to bind to various molecular targets such as small molecules, proteins, nucleic acids, and even cells, tissues and organisms. Aptamers offer molecular recognition properties that rival those of antibodies. In addition, aptamers offer advantages over antibodies as they can be engineered completely in vitro, are readily produced by chemical synthesis, and possess desirable storage properties. Aptamers are typically created by the SELEX (Systematic Evolution of Ligands by Exponential Enrichment) process and variations upon it. The SELEX process is described in, for example, U.S. Pat. Nos. 5,270,163 and 5,475,096 (both of which are incorporated by reference).

D. Kits

Any of the compositions described herein may be comprised in a kit. For example, the kits may comprise suitably aliquoted magnetic and/or labeled antibody compositions of the present invention, as may be used to isolate, separate, or detect a targeted cell or population of cells. It may also include one or more buffers, such as hybridization buffer or a wash buffer. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional containers into which the additional components may be separately placed. However, various combinations of components may be comprised in a vial. The kits of the present invention also will typically include a means for containing the antibodies, and any other reagent containers in close confinement for commercial sale. Such containers may include cardboard or injection or blow-molded plastic containers into which the desired vials, bottles, etc. are retained.

When the components of the kit are provided in one or more liquid solutions, the liquid solution may be an aqueous solution, with a sterile aqueous solution being particularly preferred.

However, certain components of the kit may be provided as dried powder(s). When reagents and/or components are provided as a dry powder, the powder can be reconstituted by the addition of a suitable solvent. It is envisioned that the solvent may also be provided in another container means.

A kit may also include instructions for employing the kit components. Instructions may include variations that can be implemented.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Enumeration of CD4 Cells

In this example the magnetic capturing antibody is an Anti-CD4 antibody that captures all CD4 lymphocytes as well as all CD4 monocytes. The detecting antibody is the same or another anti-CD4 antibody conjugated with a fluorescent label. The real-time analysis process monitors the population of CD4 cells present in the imaging chamber. At the end of the sample loading step, all enumerated CD4 cells will correspond to all CD4 lymphocytes and CD4 monocytes captured by the capturing antibody and labeled by the detecting antibody.

A sample of whole blood is collected and stored in a BD Vacutainer containing 2 mM EDTA as anticoagulant (BD Biosciences #366452). 20 µL of the sample is pipeted into a 1.5 mL centrifuge tube. 5 µL of Magnetic Anti-CD4 capturing Antibody (IMag™ Anti-human CD4 particles—BD Biosciences Cat#: 557767) are directly added to the centrifuge tube containing the 20 µL of blood sample. 5 µL of phycoerythrin (PE) labeled Anti-CD4 detecting Antibody (R-PE conjugated mouse anti human monoclonal Antibody—BD Biosciences Cat #555347) are also directly added to the centrifuge tube containing the 20 µL of blood sample. Some mixing is performed using the pipetor. The sample is incubating for 20 minutes without further mixing. The sample is diluted using 1 mL of a solution of PBS/BSA (Prepackaged PBS/BSA: Sigma P3688) and the sample is injected into the imaging chamber.

The Magnetic field of the apparatus is turned on as soon as the sample introduction is started. Successive visualization of the sample and introduction of new sample aliquots enable the decision of continuing loading more sample aliquots or ending this step. Once the loading step is completed, the enumeration of the cells in the field of view of the imaging chamber is performed and the number of cells per microliter of sample is calculated according to the volume of sample loaded, the ratio of the size of the field of view to the size of the surface of the imaging chamber subjected to the magnetic field, and the capture efficiency of the apparatus.

Example 2

Enumeration of CD4 Lymphocytes by Subtractive Strategy

In this example the magnetic capturing antibody is an anti-CD4 antibody that captures all CD4 lymphocytes as well as all CD4 monocytes. The cocktail of detection antibodies will include an anti-CD4 antibody conjugated with one fluorescent label (Label 1), and an anti-CD14 antibody conjugated to another fluorescent label (Label 2). The real-time analysis process will monitor the population of CD4 cells present in the imaging chamber. At the end of the sample loading step, all enumerated CD4 cells will correspond to all CD4 lymphocytes and CD4 monocytes captured by the capturing antibody and present in the sample. All enumerated CD14 cells will correspond only to the population of monocytes captured by the capturing antibody and present in the sample. The count of CD4 lymphocytes is calculated by deduction of the monocytes count from the total CD4 count.

A sample of whole blood is collected and stored in a BD Vacutainer containing 2 mM EDTA as anticoagulant (BD Biosciences #366452). 20 µL of the sample is pipeted into a 1.5 mL centrifuge tube. 5 µL of magnetic anti-CD4 capturing antibody are directly added to the centrifuge tube containing the 20 µL of blood sample. 5 µL of anti-CD4 detecting antibody labeled with a fluorescent molecule compatible with the reading apparatus are also directly added to the centrifuge tube containing the 20 µL of blood sample. 5 µL of anti-CD14 detecting antibody, labeled with a fluorescent molecule different from the previous one and also compatible with the reading apparatus, are also directly added to the centrifuge tube containing the 20 µL of blood sample. Some mixing is performed using the pipetor. The sample is incubated for 20 minutes without further mixing. The sample is diluted using 1 mL of a solution of PBS/BSA (Prepackaged PBS/BSA: Sigma P3688) and presented to the injection syringe of the reading instrument. Aliquots of the sample are injected into the imaging chamber.

The magnetic field of the apparatus is turned on as soon as the sample introduction is started. Successive visualization of the sample (using the detection channel dedicated to the CD4 fluorescent label) and introduction of new sample aliquots enable the decision of continuing loading more sample aliquots or ending this step. Once the loading step is completed, the enumerations of the CD4 and CD14 cells in the field of view of the imaging chamber are performed sequentially using two detection channels of the apparatus. The numbers of cells per microliter of sample are calculated according to the volume of sample loaded, the ratio of the size of the field of view to the size of the surface of the imaging chamber subjected to the magnetic field, and the capture efficiency of the apparatus.

Example 3

Figure 7:
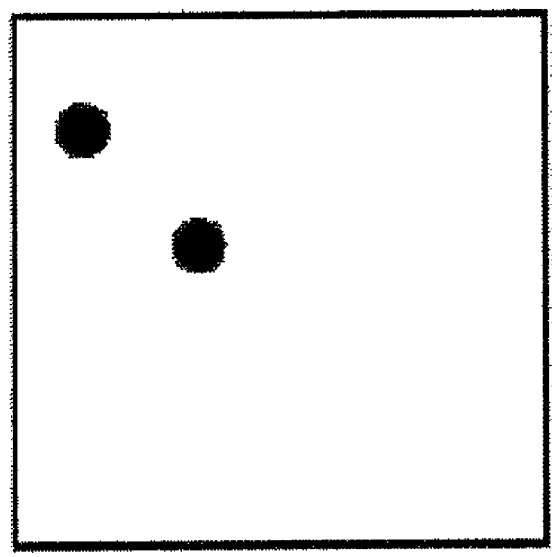
FIG. 7 is an illustration of an imaging system's field of view at various time points during sample loading.
Figure 7:
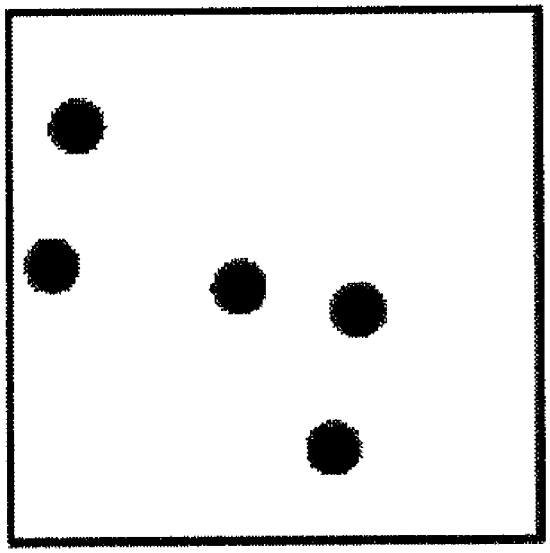
Figure 7:
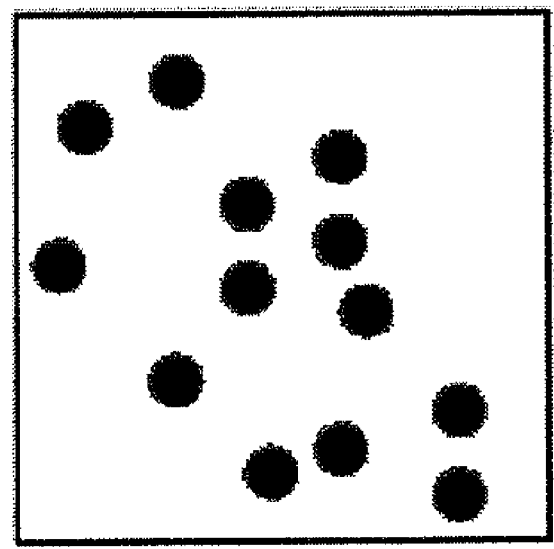
Figure 7:
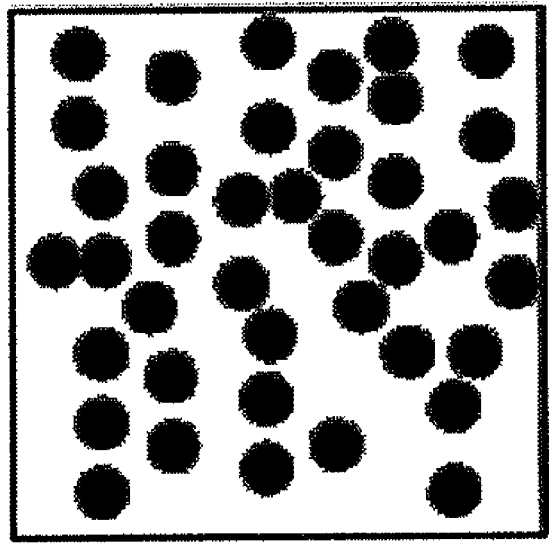
Figure 8A:
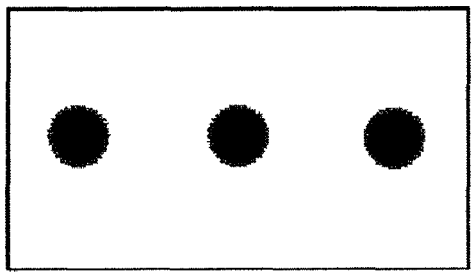
FIGS. 8A, 8B, and 8C are illustrations of images obtained with three detection channels.
Figure 8B:
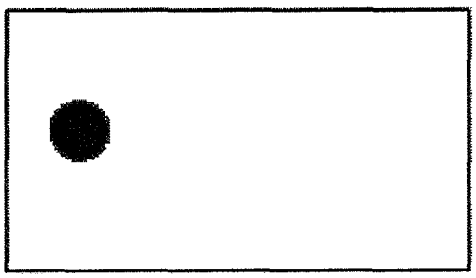
Figure 8C:
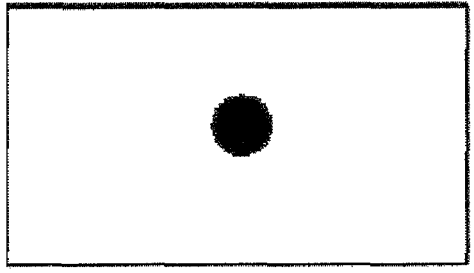

Measurement of Clinically Relevant Counts of CD3 Cells, CD4 Cells, and CD8 Cells In this example the magnetic capturing antibody is an anti-CD3 antibody that captures all lymphocytes. The cocktail of detection antibodies includes an anti-CD3 antibody conjugated with one fluorescent label (Label 1), and an anti-CD4 antibody conjugated to another fluorescent label (Label 2) and an anti-CD8 antibody conjugated to a third fluorophore (Label 3). The real-time analysis process monitors the population of CD3 cells present in the imaging chamber. FIG. 7 illustrates the imaging systems field of view using the "Label 1" detection channel, which detects the CD3 population (i.e., all lymphocytes), at time points T1, T2, . . . Tn, and Tfinal. Detection and enumeration of the captured cells is repeatedly performed until the imaging processing algorithm enumerates a number of cells above a certain threshold. Once the number of cells in the field of view reaches the defined threshold, the sample loading sequence is ended. At the end of the sample loading step, three readings are performed in each of the three detection channels dedicated to one of the three fluorophores. The Label 1 detection channel, dedicated to the fluorescent Label 1, will enumerate all CD3 cells which correspond to all lymphocytes as illustrated in FIG. 8A. The Label 2 detection channel will enumerate the CD4 subpopulation of lymphocytes as illustrated in FIG. 8B. Finally the Label 3 detection channel will enumerate the CD8 subpopulation of lymphocytes as illustrated in FIG. 8C. The CD4 to CD8 Ratio and percentage of CD3 cells being also CD4 cells can be calculated from the three measurements.

A sample of whole blood is collected and stored in a BD Vacutainer containing 2 mM EDTA as anticoagulant (BD Biosciences #366452). 20 μL of the sample is pipeted into a 1.5 mL centrifuge tube. 5 μL of Magnetic anti-CD3 capturing antibody are directly added to the centrifuge tube containing the 20 μL of blood sample. 5 μL of anti-CD3 detecting antibody labeled with a fluorescent molecule (Label 1) compatible with the reading apparatus are also directly added to the centrifuge tube containing the 20 μL of blood sample. 5 μL of anti-CD4 detecting antibody, labeled with a second fluorescent molecule (Label 2) different from the previous one and also compatible with the reading apparatus, are also directly added to the centrifuge tube containing the 20 μL of blood sample. 5 μL of anti-CD8 detecting antibody, labeled with a third fluorescent molecule (Label 3) different from the previous two and also compatible with the reading apparatus, are also directly added to the centrifuge tube containing the 20 μL of blood sample. Some mixing is performed using the pipetor. The sample is incubated for 20 minutes without further mixing. The sample is diluted using 1 mL of a solution of PBS/BSA (Prepackaged PBS/BSA: Sigma P3688) and presented to the injection syringe of the reading instrument. Aliquots of the sample are injected into the imaging chamber.

The magnetic field of the apparatus is turned on as soon as the sample introduction is started. Successive visualization of the sample (using the detection channel dedicated to the CD3 fluorescent label) and introduction of new sample aliquots enable the decision of continuing loading more sample aliquots or ending this step. Once the loading step is completed, the enumerations of the CD3, CD4 and CD8 cells in the field of view of the imaging chamber are performed sequentially using three detection channels of the apparatus. The numbers of cells per microliter of sample are calculated according to the volume of sample loaded, the ratio of the size of the field of view to the size of the surface of the imaging chamber subjected to the magnetic field, and the capture efficiency of the apparatus.

Example 4

Separation and Detection of CD4 Cells from Whole Blood 1 mL of PBS/BSA was added to a BD Vacutainer containing 2 mM EDTA as anticoagulant (BD Biosciences #366452). 20 μL of the PBS/BSA/EDTA was transferred to a 1.5 mL centrifuge tube. Using a sterile finger prick, 1 or 2 drops of blood were collected directly into the 1.5 mL centrifuge tube. 1 or 5 μL of magnetic anti-CD4 capturing antibody (IMag™ anti-human CD4 particles (BD Biosciences Cat#:557767)) was added to the centrifuge tube containing the blood sample. 1 or 5 μL of anti-CD4 detecting antibody labeled with a fluorescent molecule (R-PE conjugated mouse anti-human monoclonal antibody (BD Biosciences Cat#: 555347)) compatible with the reading apparatus was also added to the centrifuge tube containing the blood sample. Some mixing was performed using the pipetor. The samples were incubated for 20-25 minutes without further mixing. The samples were diluted using 1 mL, 400 μL, or 200 μL of a solution of PBS/BSA (Prepackaged PBS/BSA: Sigma P3688) and presented to the injection syringe of the reading instrument. Aliquots of the sample are injected into the imaging chamber. The sample prep matrix is shown in Table 1.

TABLE 1

| | Sample # | | |
|---|---|---|---|
| | 1 | 2 | 3 |
| Blood | 1 drop | 1 drop | 2 drops |
| EDTA Buffer | 30 μl | 10 μl | 20 μl |
| Capturing Ab | 1 μl | 5 μl | 5 μl |
| Detecting Ab | 1 μl | 5 μl | 5 μl |
| Incubation Time | 25 minutes | 25 minutes | 20 minutes |
| PBS Buffer | 1 ml | 200 μl | 400 μl |

Figure 9:
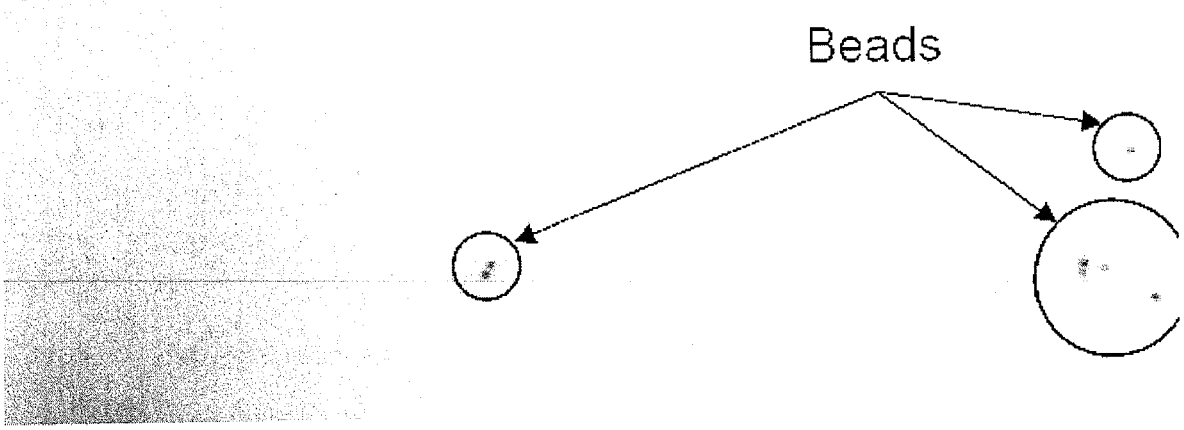
FIG. 9 is an inverted image obtained with the classification channel showing labeled beads.
Figure 10:
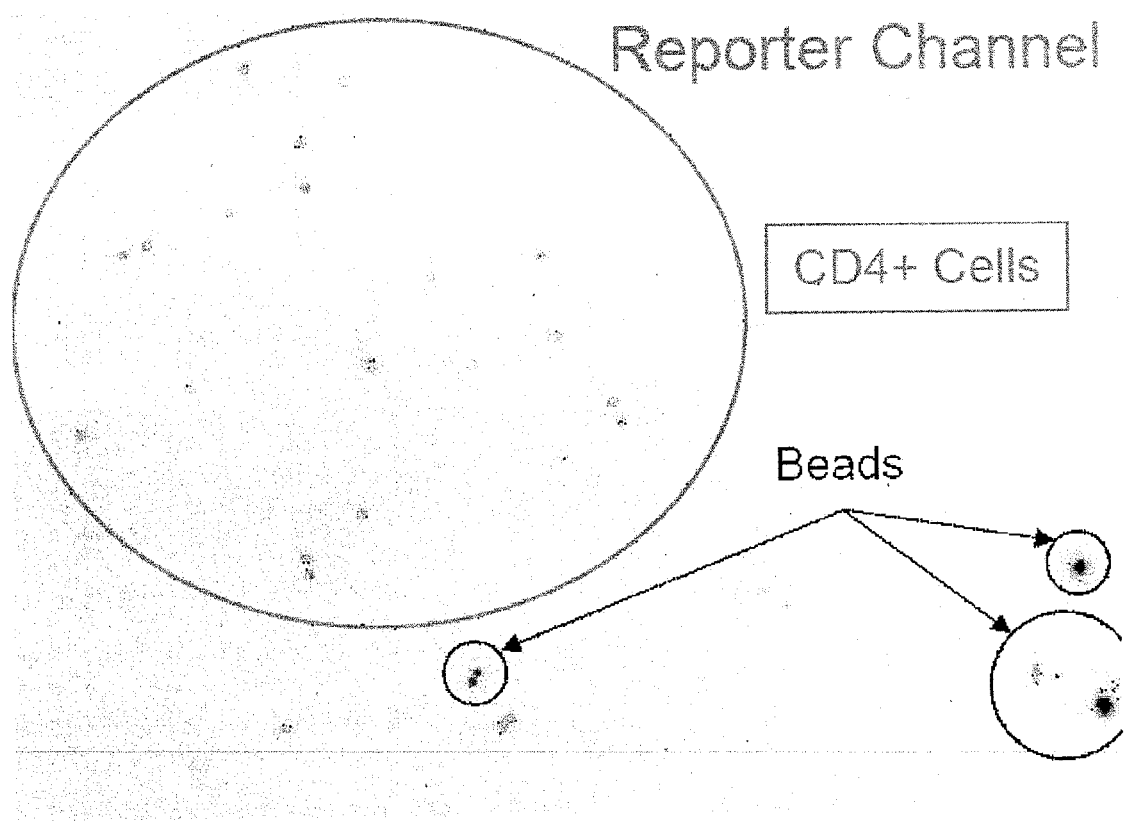
FIG. 10 is an inverted image obtained with the reporter channel showing labeled CD4+ cells and labeled beads.

The imaging instrument was initialized using calibration beads developed at Luminex according to the method described prior art by Chandler and al. (U.S. Pat. No. 6,632,526). These calibration beads express a fluorescent signal in each detection channel to enable autofocus of the system. After a wash sequence some beads remained in the chamber and were used to localize a specific area of the field of view. The magnetic field of the apparatus was turned on as soon as the sample introduction started. Despite the high viscosity of the sample, cells were sufficiently magnetized by the capturing magnetic antibody to be attracted by the magnetic field and immobilized on the imaging chamber surface. The labeled cells were imaged using the green excitation LEDs and the reporter detection channel. Beads remaining in the imaging chamber were also imaged using the green LED and the reporter detection channel. In addition, beads were imaged using the red LEDs as the excitation source and the CL1 detection channel. The beads appear in both images because they contain both classification and reporter dyes. CD4 specific cells appear only in the reporter channel. Inverted images from the classification channel and reporter channel are shown in FIGS. 9 and 10, respectively. No signal from CD4 cells was detected in sample 1, but signals from the CD4 cells were detected in samples 2 and 3.

This study showed that the imaging system was able to attract cells rendered magnetically responsive by binding them to antibodies coated with magnetic nanoparticles (size: 100 to 400 nM). The cells were labeled by both the capturing and detecting antibodies directly within the sample matrix, and little was done to increase the kinetic of the binding. The only mixing was done when adding the antibodies and using the pipette functionality to mix the sample and reagent mix.

Example 5

Sequential Loading of Multiple Sample Aliquots

Figure 11:
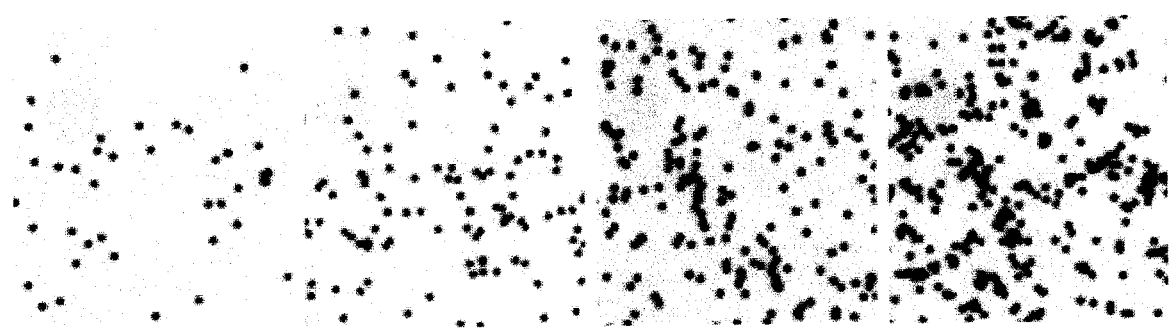
FIG. 11 is a sequence of inverted images showing the increase in the density of objects in the filed of view as additional sample aliquots are introduced into the imaging chamber.

To demonstrate the sequential loading of multiple sample aliquots, a solution of fluorescent beads was prepared at a concentration of 29,900 beads per mL. The initial aliquot loaded was 50 μL. Once the first aliquot was in the chamber and under the influence of the magnetic field, a wash of the sample matrix was performed using the by-pass line. Then the imaging system collected images of the sample. Without removing the first aliquot from the chamber, a second 50 μL aliquot was introduced in the chamber as well, and again a wash of the sample matrix was performed using the by-pass line. This process was repeated until 8 aliquots were injected in the chamber. FIG. 11 shows a small and magnified portion of the collected pictures for Aliquots 1, 3, 6 and 8. An increase in bead counts is seen as more 50 μL aliquots are injected into the imaging chamber. Eventually, as the picture of sample 8 shows, too much sample resulted in an overlap of the target objects which appeared as large aggregates. This illustrates the need for an upper limit threshold that will prevent an overload of the sample.

Example 6

Loading of a Highly Concentrated Sample

Figure 12:
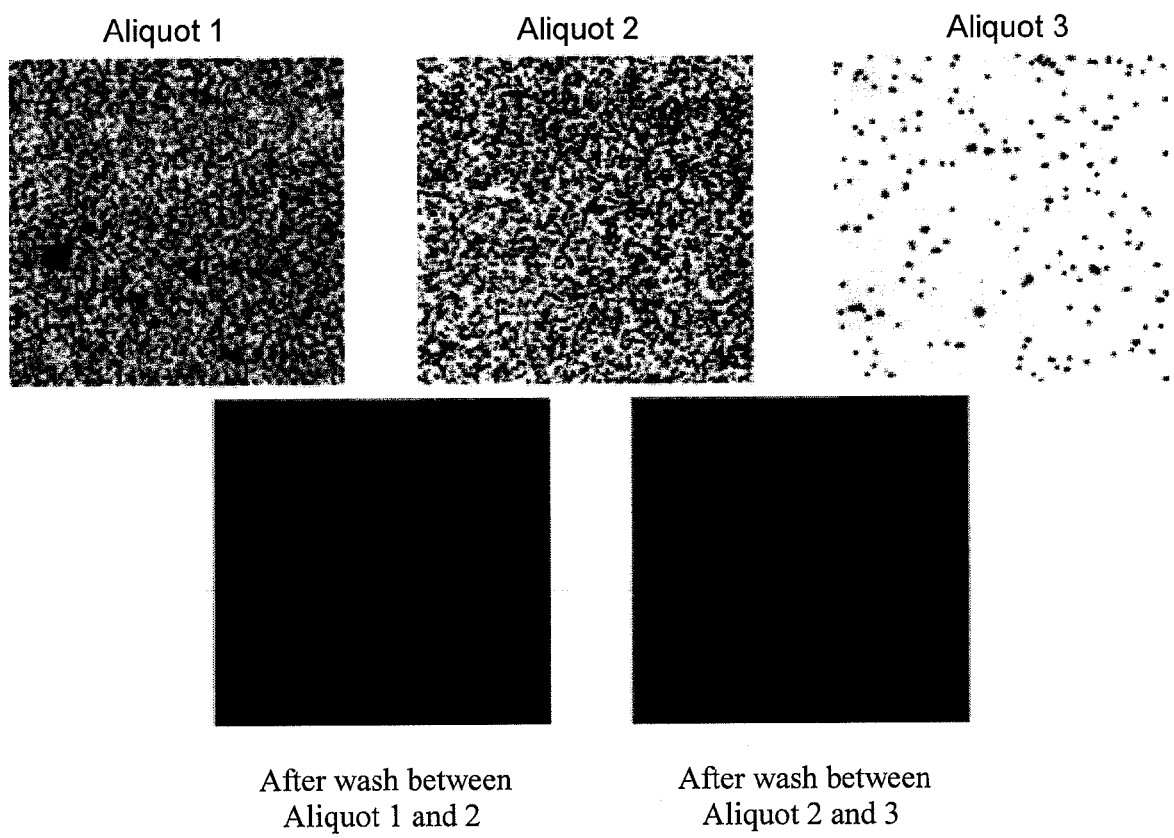
FIG. 12 is a sequence of inverted images showing the imaging of a highly concentrated sample. Aliquot 1 is too concentrated to be analyzed properly. After a complete wash of the imaging chamber, a second aliquot, which was a third the size of Aliquot 1, was loaded into the chamber. Aliquot 2 was also too concentrated to be analyzed properly. After another complete wash of the imaging chamber, a third aliquot, which was ⅙ the size of Aliquot 1, was introduced into the chamber. Aliquot 3 resulted in a concentration of objects in the chamber that was acceptable for further processing.

To demonstrate the handling of highly concentrated samples, a solution of fluorescent beads at a concentration of 29.9 million beads per mL was prepared. The initial aliquot loaded was 50 μL. Once the first aliquot was in the chamber and under the influence of the magnetic field, a wash of the sample matrix was performed using the by-pass line. Then the imaging system collected images of the sample. FIG. 12 shows a small and magnified portion of the collected pictures for Aliquot 1, 2, and 3, as well as images of the chamber in between aliquots. As the first aliquot appeared too concentrated, the magnetic field was removed and the chamber was completely emptied and washed using the by-pass line. Meanwhile the unused portion of the sample remained untouched in the sample loop. The lower images in FIG. 12 were taken right after this regeneration step and are a confirmation of the complete wash of the chamber. Then, the magnetic field was reapplied and a smaller aliquot (17 μL) was injected into the chamber. Using the by-pass line, a wash of the sample matrix was performed. This aliquot appeared too concentrated as well. The magnetic field was removed and again the chamber was completely cleaned using the bypass line while what was left of the sample stays in the sample loop (The second lower image from FIG. 12 shows the efficiency of the wash). Last, the magnetic field was reapplied and a third and smaller aliquot (8 μL) was pushed from the sample loop into the chamber. This aliquot brought enough beads in the chamber to perform an accurate analysis and enumeration.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Bioinformatics Market Research 2006 Report #06-030: influencing brand preference in the flow cytometry market
The Cell—A molecular approach; Geoffrey M. Cooper. ASM Press. 1997
U.S. Pat. No. 4,196,265
U.S. Pat. No. 5,270,163
U.S. Pat. No. 5,475,096
U.S. Pat. No. 6,632,526
U.S. patent application Ser. No. 11/534,166
U.S. patent application Ser. No. 11/757,841

The invention claimed is:

1. A method for immobilizing and detecting a cell in a sample comprising:
    (a) contacting a sample with a magnetic antibody having a specific affinity for a particular epitope on a first cell that may be present in the sample;
    (b) contacting the sample with a first labeled antibody having a specific affinity for a particular epitope on the cell;
    (c) introducing an aliquot of the sample into a chamber;
    (d) applying a magnetic field to the chamber to attract the magnetic antibody to a surface of the chamber;
    (e) washing the chamber to remove the portion of the sample that is not immobilized on the surface of the chamber by binding the magnetic antibody;
    (f) detecting and enumerating the cells that are immobilized on the surface of the chamber by binding the magnetic antibody and labeled by binding the labeled antibody;
    (g) determining whether a statistically significant number of the labeled cells are immobilized on the surface of the chamber for detecting and enumerating;
    (h) repeating steps (c) to (g) until a statistically significant number of the labeled cells are immobilized on the surface of the chamber; and
    (i) detecting and enumerating the immobilized and labeled cells.

2. The method of claim 1, wherein the sample is a bodily fluid.

3. The method of claim 1, wherein the sample is an environmental sample.

4. The method of claim 1, wherein the cell is a lymphocyte, leukocyte, or monocyte.

5. The method of claim 1, wherein the cell is a bacteria cell, a spore, or a fungus cell.

6. The method of claim 1, wherein the magnetic antibody and the labeled antibody have a specific affinity for the same epitope.

7. The method of claim 1, wherein the magnetic antibody and the labeled antibody have a specific affinity for different epitopes.

8. The method of claim 1, wherein the sample is contacted with the labeled antibody prior to introducing the sample into the chamber.

9. The method of claim 1, wherein the sample is contacted with the labeled antibody after introducing the sample into the chamber.

10. The method of claim 1, wherein the labeled antibody is a fluorescently labeled antibody.

11. The method of claim 1, further comprising correlating the number of cells detected with the number of cells in the sample.

12. The method of claim 1, further comprising contacting the sample with a second labeled antibody having a specific affinity for a particular epitope on the cell prior to washing the chamber, wherein the second labeled antibody is labeled with a label different than the label of the first labeled antibody.

13. The method of claim 12, wherein the first labeled antibody and the second labeled antibody have specific affinity to different epitopes present on different cell populations.

14. The method of claim 1, further comprising:
    contacting the sample with a plurality of different magnetic antibodies having a specific affinity for particular epitopes on a plurality of different cells that may be present in the sample prior to applying the magnetic field to the chamber; and contacting the sample with a plurality of different labeled antibodies having specific affinities for particular epitopes on the plurality of different cells prior to washing the chamber.

15. A method for immobilizing and detecting one or more cell populations and/or subpopulations in a sample comprising:
   (a) contacting a sample with a magnetic antibody having a specific affinity for a particular epitope on a cell population that may be present in the sample;
   (b) contacting the sample with a first labeled antibody having a specific affinity for a particular epitope on the cell population;
   (c) contacting the sample with a second labeled antibody having a specific affinity for a particular epitope on a first subpopulation of cells in the cell population;
   (d) contacting the sample with a third labeled antibody having a specific affinity for a particular epitope on a second subpopulation of cells in the cell population;
   (e) introducing an aliquot of the sample into a chamber;
   (f) applying a magnetic field to the chamber to attract the magnetic antibody to a surface of the chamber;
   (g) washing the chamber to remove the portion of the sample that is not immobilized on the surface of the chamber by binding the magnetic antibody;
   (h) detecting and enumerating the cells that are immobilized on the surface of the chamber by binding the magnetic antibody and labeled by binding the first labeled antibody;
   (i) determining whether a statistically significant number of the labeled cells are immobilized on the surface of the chamber for detecting and enumerating;
   (j) repeating steps (e) to (i) until a statistically significant number of the labeled cells are immobilized on the surface of the chamber;
   (k) detecting and enumerating the immobilized cells labeled with each of the first, second, and third labeled antibodies.

16. The method of claim 15, further comprising determining a ratio of the first subpopulation of cells to the second subpopulation of cells.

17. The method of claim 15, further comprising calculating the percentage of the first subpopulation of cells in the cell population.

18. The method of claim 15, further comprising calculating the percentage of the second subpopulation of cells in the cell population.

19. The method of claim 15, further comprising determining the concentration of the cell population in the sample.

20. The method of claim 15 further comprising:
   contacting the sample with a fourth labeled antibody having a specific affinity for a particular epitope on a third subpopulation of cells in the cell population prior to washing the chamber; and
   detecting and enumerating the immobilized cells labeled with fourth labeled antibody after the statistically significant number of cells are immobilized on the surface of the chamber.

21. The method of claim 20 further comprising:
   contacting the sample with a fifth labeled antibody having a specific affinity for a particular epitope on a fourth subpopulation of cells in the cell population prior to washing the chamber;
   contacting the sample with a sixth labeled antibody having a specific affinity for a particular epitope on a fifth subpopulation of cells in the cell population prior to washing the chamber;
   contacting the sample with a seventh labeled antibody having a specific affinity for a particular epitope on a sixth subpopulation of cells in the cell population prior to washing the chamber;
   contacting the sample with a eighth labeled antibody having a specific affinity for a particular epitope on a seventh subpopulation of cells in the cell population prior to washing the chamber; and
   detecting and enumerating the immobilized cells labeled with the fifth, sixth, seventh, and eighth labeled antibodies after the statistically significant number of cells are immobilized on the surface of the chamber.

22. The method of claim 21, further comprising calculating the percentages of the third, fourth, fifth, sixth, and seventh subpopulations of cells in the cell population.

* * * * *